United States Patent
Papadimitriou

(10) Patent No.: US 7,169,754 B2
(45) Date of Patent: *Jan. 30, 2007

(54) ERYTHROPOIETIN COMPOSITION

(75) Inventor: Apollon Papadimitriou, Bichl (DE)

(73) Assignee: Hoffmann-la Roche Inc., Nutley, NJ (US)

( * ) Notice: Subject to any disclaimer, the term of this patent is extended or adjusted under 35 U.S.C. 154(b) by 800 days.

This patent is subject to a terminal disclaimer.

(21) Appl. No.: 09/853,731

(22) Filed: May 11, 2001

(65) Prior Publication Data

US 2002/0037841 A1 Mar. 28, 2002

(30) Foreign Application Priority Data

May 15, 2000 (EP) ................... 00110355

(51) Int. Cl.
C07K 17/00 (2006.01)
A61K 38/17 (2006.01)

(52) U.S. Cl. ................ 514/8; 514/12; 514/21; 514/970; 530/350; 530/397; 435/69.1; 435/320.1; 435/325

(58) Field of Classification Search ........... 514/8, 514/12, 21, 970; 530/350, 397; 435/69.1, 435/320.1, 325
See application file for complete search history.

(56) References Cited

U.S. PATENT DOCUMENTS

| | | | |
|---|---|---|---|
| 4,732,889 A | 3/1988 | Cynshi et al. | |
| 4,806,524 A | 2/1989 | Kawaguchi et al. | |
| 4,992,419 A | 2/1991 | Woog et al. | |
| 5,099,003 A | 3/1992 | Kotitschke et al. | |
| 5,272,135 A | 12/1993 | Takruri | |
| 5,354,934 A | 10/1994 | Pitt et al. | |
| 5,460,944 A | 10/1995 | Franken et al. | |
| 5,661,125 A | 8/1997 | Strickland | |
| 5,716,644 A | 2/1998 | Zale et al. | |
| 5,981,707 A | 11/1999 | Harrington et al. | |
| 6,120,761 A | 9/2000 | Yamazaki et al. | |
| 6,277,367 B1 | 8/2001 | Yamazaki et al. | |
| 6,340,742 B1 * | 1/2002 | Burg et al. | 530/351 |
| 6,372,715 B1 | 4/2002 | Kaltwasser et al. | |
| 6,440,932 B1 | 8/2002 | Lehmann et al. | |
| 6,586,398 B1 | 7/2003 | Kinstler et al. | |
| 6,627,187 B2 | 9/2003 | Yamazaki et al. | |
| 6,696,056 B1 | 2/2004 | Cheung et al. | |
| 6,818,613 B2 | 11/2004 | Sharma et al. | |
| 2002/0115833 A1 * | 8/2002 | Burg et al. | 530/395 |
| 2003/0092622 A1 | 5/2003 | Sato et al. | |
| 2003/0104996 A1 | 6/2003 | Li et al. | |
| 2004/0038878 A1 | 2/2004 | Tanikawa et al. | |
| 2004/0147431 A1 * | 7/2004 | Papadimitriou | 514/8 |
| 2004/0248797 A1 | 12/2004 | Cheung et al. | |

FOREIGN PATENT DOCUMENTS

| | | |
|---|---|---|
| DE | 41 35 542 | 4/1993 |
| EP | 0178665 | 4/1986 |
| EP | 0456153 | 11/1991 |
| EP | 539167 A2 | 4/1993 |
| EP | 0640619 * | 3/1995 |
| EP | 0909564 | 4/1999 |
| EP | 1232753 A1 | 8/2002 |
| GB | 2171304 | 8/1986 |
| WO | WO-9206116 * | 4/1992 |
| WO | WO 94/20069 | 9/1994 |
| WO | WO 94/28024 A1 | 12/1994 |
| WO | WO 95/11924 A1 | 5/1995 |
| WO | WO 96/40073 | 12/1996 |
| WO | WO 98/05363 A2 | 2/1998 |
| WO | 00/24893 | 5/2000 |
| WO | WO 00/27419 A1 | 5/2000 |
| WO | 01/07075 | 2/2001 |
| WO | WO 01/12155 | 2/2001 |
| WO | WO 03/020299 | 3/2003 |

* cited by examiner

*Primary Examiner*—Chih-Min Kam
(74) *Attorney, Agent, or Firm*—George W. Johnston; Patricia S. Rocha-Tramaloni

(57) ABSTRACT

The present invention relates to a liquid pharmaceutical composition comprising an erythropoietin protein, a multiple charged inorganic anion in a pharmaceutically acceptable buffer suitable to keep the solution pH in the range from about 5.5 to about 7.0, and optionally one or more pharmaceutically acceptable excipients. This composition is especially useful for the prophylaxis and treatment of diseases related to erythropoiesis.

58 Claims, 6 Drawing Sheets

Figure 1

Ala Pro Pro Arg Leu Ile Cys Asp Ser Arg$^{10}$ Val Leu Glu Arg Tyr Leu Leu Glu Ala Lys$^{20}$
Glu Ala Glu Asn Ile Thr Thr Gly Cys Ala$^{30}$ Glu His Cys Ser Leu Asn Glu Asn Ile Thr$^{40}$
Val Pro Asp Thr Lys Val Asn Phe Tyr Ala$^{50}$ Trp Lys Arg Met Glu Val Gly Gln Gln Ala$^{60}$
Val Glu Val Trp Gln Gly Leu Ala Leu Leu$^{70}$ Ser Glu Ala Val Leu Arg Gly Gln Ala Leu$^{80}$
Leu Val Asn Ser Ser Gln Pro Trp Glu Pro$^{90}$ Leu Gln Leu His Val Asp Lys Ala Val Ser$^{100}$
Gly Leu Arg Ser Leu Thr Thr Leu Leu Arg$^{110}$ Ala Leu Gly Ala Gln Lys Glu Ala Ile Ser$^{120}$
Pro Pro Asp Ala Ala Ser Ala Ala Pro Leu$^{130}$ Arg Thr Ile Thr Ala Asp Thr Phe Arg Lys$^{140}$
Leu Phe Arg Val Tyr Ser Asn Phe Leu Arg$^{150}$ Gly Lys Leu Lys Leu Tyr Thr Gly Glu Ala$^{160}$
Cys Arg Thr Gly Asp$^{165}$

Figure 2

Ala Pro Pro Arg Leu Ile Cys Asp Ser Arg$^{10}$ Val Leu Glu Arg Tyr Leu Leu Glu Ala Lys$^{20}$
Glu Ala Glu Asn Ile Thr Thr Gly Cys Ala$^{30}$ Glu His Cys Ser Leu Asn Glu Asn Ile Thr$^{40}$
Val Pro Asp Thr Lys Val Asn Phe Tyr Ala$^{50}$ Trp Lys Arg Met Glu Val Gly Gln Gln Ala$^{60}$
Val Glu Val Trp Gln Gly Leu Ala Leu Leu$^{70}$ Ser Glu Ala Val Leu Arg Gly Gln Ala Leu$^{80}$
Leu Val Asn Ser Ser Gln Pro Trp Glu Pro$^{90}$ Leu Gln Leu His Val Asp Lys Ala Val Ser$^{100}$
Gly Leu Arg Ser Leu Thr Thr Leu Leu Arg$^{110}$ Ala Leu Gly Ala Gln Lys Glu Ala Ile Ser$^{120}$
Pro Pro Asp Ala Ala Ser Ala Ala Pro Leu$^{130}$ Arg Thr Ile Thr Ala Asp Thr Phe Arg Lys$^{140}$
Leu Phe Arg Val Tyr Ser Asn Phe Leu Arg$^{150}$ Gly Lys Leu Lys Leu Tyr Thr Gly Glu Ala$^{160}$
Cys Arg Thr Gly Asp Arg$^{166}$ 1  2  3  4  5  6  7  8  9  10

}higher order aggregates

}aggregates
}dipeg-EPO

}monopeg-EPO 1    2    3    4    5    6

}aggregates
}dipeg-EPO

}monopeg-EPO

ERYTHROPOIETIN COMPOSITION

This application claims priority of European Patent Office Application No. 00110355.5, filed May 15, 2000.

BACKGROUND OF THE INVENTION

Erythropoiesis is the production of red blood cells, which occurs to offset cell destruction. Erythropoiesis is a controlled physiological mechanism that enables sufficient red blood cells to be available for proper tissue oxygenation. Naturally occurring human erythropoietin (hEPO) is produced in the kidney and is the humoral plasma factor which stimulates red blood cell production (Carnot, P and Deflandre, C (1906) C. R. Acad. Sci. 143: 432; Erslev, AJ (1953) Blood 8: 349; Reissmann, KR (1950) Blood 5: 372; Jacobson, LO, Goldwasser, E, Freid, W and Plzak, LF (1957) Nature 179: 6331–4). Naturally occurring EPO stimulates the division and differentiation of committed erythroid progenitors in the bone marrow and exerts its biological activity by binding to receptors on erythroid precursors (Krantz, BS (1991) Blood 77: 419).

Erythropoietin has been manufactured biosynthetically using recombinant DNA technology (Egrie, JC, Strickland, TW, Lane, J et al. (1986) Immunobiol. 72: 213–224) and is the product of a cloned human EPO gene inserted into and expressed in the ovarian tissue cells of the chinese hamster (CHO cells). The primary structure of the predominant, fully processed form of hEPO is illustrated in SEQ ID NO: 1. There are two disulfide bridges between $Cys^7$–$Cys^{161}$ and $Cys^{29}$–$Cys^{33}$. The molecular weight of the polypeptide chain of EPO without the sugar moieties is 18,236 Da. In the intact EPO molecule, approximately 40% of the molecular weight are accounted for by the carbohydrate groups that glycosylate the protein at glycosylation sites on the protein (Sasaki, H, Bothner, B, Dell, A and Fukuda, M (1987) J. Biol. Chem. 262: 12059).

Because human erythropoietin is essential in red blood cell formation, the hormone is useful in the treatment of blood disorders characterized by low or defective red blood cell production. Clinically, EPO is used in the treatment of anemia in chronic renal failure patients (CRF) (Eschbach, JW, Egri, JC, Downing, MR et al. (1987) NEJM 316: 73–78; Eschbach, JW, Abdulhadi, MH, Browne, JK et al. (1989) Ann. Intern. Med. 111: 992; Egrie, JC, Eschbach, JW, McGuire, T, Adamson, JW (1988) Kidney Intl. 33: 262; Lim, VS, Degowin, RL, Zavala, D et al. (1989) Ann. Intern. Med. 110: 108–114) and in AIDS and cancer patients undergoing chemotherapy (Danna, RP, Rudnick, SA, Abels, RI In: MB, Garnick, ed. Erythropoietin in Clinical Applications-An International Perspective. New York, N.Y.: Marcel Dekker; 1990: p. 301–324).

Known pharmaceutical compositions have at least one of the following disadvantages:
  they are lyophilisates. Besides the complicated manufacturing procedure, lyophilisates have the disadvantage that they have to be reconstituted before injection into humans. This makes additional handling by medical personnel necessary, which is inconvenient and bears the risk of incorrect handling of the pharmaceutical product;
  they contain human serum albumin as an additive. As human serum albumin is a product derived from human body fluid, there is a risk of viral infections by contaminants in the albumin preparation. Also, allergic reactions are possible;
  all presently commercially available erythropoietin compositions are unstable at elevated temperatures, i.e. above refrigerator temperature which is usually between 2 and 8° C. Therefore, they have to be stored in a refrigerator (2–8° C.) and cannot be stored at room temperature (around 20° C.). This leads to increased costs, caused by storage and shipment at low temperature and also causes inconvenience in handling of the drug product. Unstable in this context means that storage at elevated temperatures, e.g. 25° C. for a prolonged period of time (i.e. several months, or more than 6 months) leads to degradation of the protein. Degradation in this context describes physical changes (e.g. aggregation or denaturation) and chemical changes (e.g. oxidation or modification of chemical bonds in general) of the protein molecule which are known to occur preferably at elevated temperatures (above 8° C.). Incubating a protein near or above its transition temperature (which is also called melting temperature) leads to unfolding of the protein, i.e. the native structure and the biological activity of the polypeptide is lost. The transition temperature is strongly correlated with the temperature stability of the protein and is dependent on the environment of the protein (e.g. pH, salts, ionic strength, buffer substance, etc.) For example, denaturation may lead to aggregation of erythropoietin molecules, i.e. formation of dimers (covalent or non-covalent), higher order aggregates and even particulates. This leads to reduced potency of the drug and might induce unwanted side effects after injection into humans.

The problem underlying the present invention is therefore to provide a composition which is able to minimize or suppress the above mentioned disadvantages.

SUMMARY OF THE INVENTION

The above problems are solved by providing a liquid pharmaceutical composition in the form of an aqueous solution comprising an erythropoietin glycoprotein product having the in vivo biological activity of causing bone marrow cells to increase production of reticulocytes and red blood cells, a multiple charged inorganic anion, a pharmaceutically acceptable buffer, said anion and said buffer being present in said solution in an amount to provide the solution with a pH of from 5.5 to about 7.0 and said product being present in said solution in a sufficient amount to provide a therapeutically effective amount of said product when the solution or a portion of said solution is administered to a patient. The composition of this invention may be stored as a lyophilisate or spray-dried powder contain the erythropoietin glycoprotein product, multiple charge inorganic anion, and pharmaceutically acceptable buffer, which lyophilisate or spray-dried powder when added to water will produce the aforementioned liquid pharmaceutical composition in the form of an aqueous solution.

DETAILED DESCRIPTION OF THE INVENTION

Among the preferred embodiments of this invention, liquid pharmaceutical compositions in the form of an aqueous solution containing from 10 μg to 10,000 μg per liter of solution of an erythropoietin glycoprotein product having the in vivo biological activity of causing bone marrow cells to increase production of reticulocytes and red blood cells, from 10 to 200 mmol per liter of said solution of a multiple charged inorganic anion and from 10 to 50 mmol per liter of said solution of a pharmaceutically acceptable buffer, said anion and said buffer being present in said solution in an amount to provide the solution with a pH of from 5.5 to about 7.0. Furthermore, lyophilisate or sprayed dried powder which produce this embodiment upon addition to water are also a preferred embodiment.

It has been surprisingly found that by formulating an erythropoietin in this liquid solution maintained at a pH of from about 5.5 to 7.0 produces a composition having improved stability at temperatures above refrigerator temperature (2–8° C.), especially at room temperature (i.e. below 25° C.) and even at higher temperatures, e.g. 40° C. This allows the liquid to be stored without cooling for a prolonged period of time, without loosing significant amounts of activity and without significant degradation.

The composition of this invention can be present as a unit dose for injectable or intravenous administration. On the other hand, the composition of this invention can be stored either in the liquid or solid forms and thereafter divided into unit dosage forms for intravenous or injectable administration. Therefore, the liquid composition of this invention can be present in amounts of as little as 0.3 ml for use as a single dosage form for administration. On the other hand, the volume of the claimed composition can be as large as 60 liters when it is stored prior to distribution in a packaged dosage form. In view of its enhanced stability, the composition of this invention can be stored in large containers so as to be later placed into packaging means suitable for distribution to doctors, patients and hospitals.

The injectable solution of this invention can be administrated by such conventional injection means as syringes which generally allow the administration from 0.3 ml. to 20 ml. of this composition as a single unit dose. On the other hand, the composition of this invention can be administered by injection utilizing ampuls which contain this composition either as a lyophilisate or as a spray dried powder which is then reconstituted in a conventional manner prior to injection. On the other hand, due to the stability of the compositions of this invention, compositions may be dispensed into unit dosage form such as vials which contain from about 0.3 ml to about 10 ml of this composition. In addition, the compositions of this invention can be administered intravenously utilizing intravenous bags. These bags contain from about 20 ml to about 500 ml of the solution depending upon the period in which the solution is to be administered to a patient. In accordance with this invention, the liquid solution of this invention can be stored in storage containers from which they can be further separated into small dosage form packages for distriution to doctos, hositals and patients. Due to the stability of the compositions of this invention, these compositions can be stored in such storage containers for long periods of time prior to administration.

Unless otherwise indicated the following definitions are set forth to illustrate and define the meaning and scope of the various terms used to describe the invention herein.

The term "multiple charged inorganic anion" refers to an inorganic anion having two or more negative charges per molecule, preferably from 2 to 3 negative charges per molecule, e.g. sulfate $SO_4^{2-}$, or a phosphate anion, i.e. hydrogenphosphate $HPO_4^{2-}$. The multiple charged inorganic anion is added to the solution to form the composition of this invention in the form of its corresponding salt, e.g. thesodium salt, the potassium salt and mixtures thereof, and/or in form of the buffer substance, e.g. phosphate buffer.

The term "isoosmolar or isotonic" refers to a solution that can be mixed with body fluids without affecting their constituents. Solutions which are isotonic with blood, such as sodium chloride 0.9%, have the same osmotic pressure as serum and they do not affect the membranes of the red blood cells. In general, solutions which are isotonic with blood are about 290 mosm/kg $H_2O$.

The term "strong inorganic acid" refers to inorganic acids which show a 20 to 100% dissociation in a 1 N solution, e.g. $H_2SO_4$.

The term "pharmaceutically acceptable" as used herein means that the buffer or salts are acceptable from a toxicity viewpoint as suitable for administration to humans.

The term "diluent" means an ingredient in a medicinal preparation which lacks pharmacological activity but is pharmaceutically necessary or desirable. For example a diluent may be a liquid for the dissolution of drug(s) to be injected, e.g. water.

The term "solvents" refers to a liquid that holds another substance in solution, i.e. dissolves it, e.g. water.

The term "preservatives" refers to a substance added to a pharmaceutical composition to prevent bacterial growth, e.g. benzalkonium chloride or benzyl alcohol.

The term "polyol" refers to any substance with multiple hydroxyl groups, including polyhydric alcohols and carbohydrates. The polyhydric alcohols include such compounds as sorbitol, mannitol and glycerol. Carbohydrates are cyclic molecules that may have a keto or aldehyde group, like e.g. sucrose or trehalose.

The term "erythropoietin protein product" refers to a protein product with the in vivo biological activity of causing bone marrow cells to increase production of reticulocytes and red blood cells and selected from the group consisting of human erythropoietin and analogs which are defined below. The term "pegylated erythropoietin (Peg-EPO or PEG-EPO)" refers to an erythropoietin protein which is covalently linked with one to three polyethylene derivatives as described below.

The term "device" means a contrivance for a specific purpose. In the present invention the purpose is to enable, support or facilitate administration of the liquid pharmaceutical composition.

Polysorbate 20 designates (Tween 20, Sigma-Aldrich) which is a polyoxythylene sorbitan ester of the formula

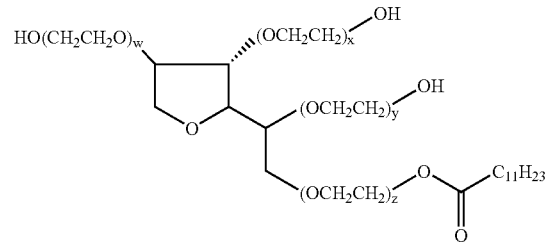

wherein the sum of w, x, y, and z is 20.

Polysorbate 80 designates (Tween 80, Sigma-Aldrich) which is a polyoxythylene sorbitan ester of the formula

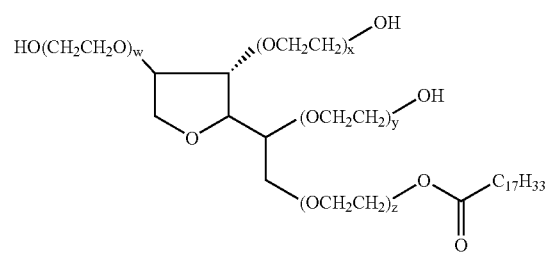

wherein the sum of w, x, y, and z is 20.

Pluronic F68 designates (BASF, Sigma-Aldrich) which is a solid copolymer consisting of hydrophobe propylene oxide and hydrophile ethylene oxide moieties. "F" indicates the physical form (solid) and the first digit (6), multiplied by 300, the approximate molecular weight of the hydrophobe moiety and the last digit (8), when multiplied by 10, indicates the approximate ethylene oxide content in the molecule The molecular weight of the hydrophobe is approximately 1800 (6×300). The hydrophile represents approximately 80% of the molecule, by weight, (8×10).

DESCRIPTION OF DRAWINGS

FIG. 1: Primary structure of human EPO (165 amino acids) (SEQ ID NO:1).

FIG. 2: Primary structure of human EPO (166 amino acids) (SEQ ID NO:2).

Figure 3:
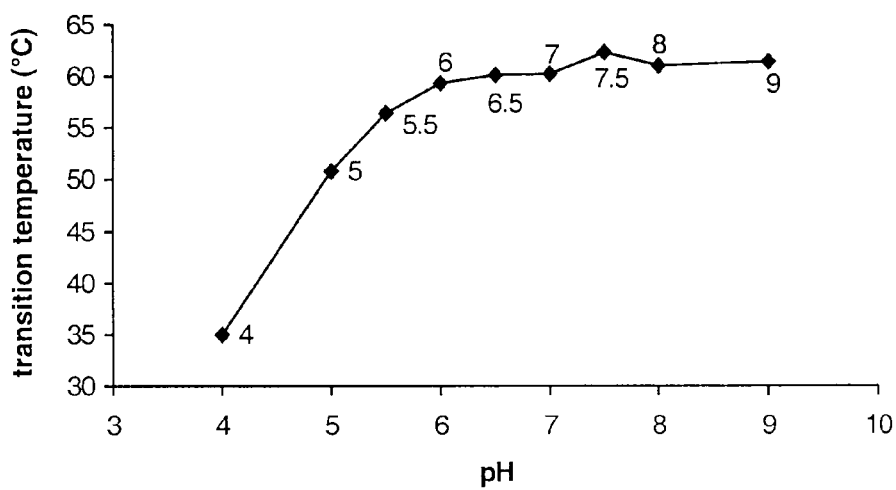
FIG. 3: Influence of pH on thermal stability. The transition temperature is plotted against the pH.

In more detail, the present invention relates to a liquid pharmaceutical composition comprising an erythropoietin protein, a multiple charged inorganic anion in a pharmaceutically acceptable buffer suitable to keep the solution pH in the range from about 5.5 to about 7.0 and optionally one or more pharmaceutically acceptable excipients.

In a preferred embodiment, the composition is a liquid solution, e.g. an aqueous solution. In a preferred embodiment of the invention, the above pharmaceutical compositions are isotonic solutions.

In accordance with this invention, any conventional multiple charged anion can be utilized. Generally, this anion contains from 2 to 3 negative charges and is added to the liquid solution in the form of its salt. The anion is preferably selected from anions of strong inorganic acids, such as $H_2SO_4$, $H_3PO_4$ or citric acid. Accordingly, preferred anions are selected from the group consisting of sulfate, phosphate and citrate, preferably sulfate or phosphate, and most preferably sulfate. The concentration of the multiple charged inorganic anion can vary from 10 and 200 mmol/l. The preferred anion is the sulfate anion at a concentration of from 10 to 200 mmol/l. As used herein, mmol/l means mmoles of compound per liter of the liquid solution of this invention.

The buffer is used in the present invention to maintain the pH in the range of about 5.5 to about 7.0, preferably in the range of 5.8 to 6.7, more preferably in the range of 6.0 to 6.5 and most preferably at about pH 6.2. This buffer can be any conventional buffer suitable for this purpose. These buffers include organic or inorganic acids (e.g., phosphate buffer, arginine/$H_2SO_4$/$Na_2SO_4$ buffer, or any other pharmaceutically acceptable buffer system). In a preferred embodiment, the composition comprises a phosphate or an arginine/$H_2SO_4$/$Na_2SO_4$ buffer, more preferably a 10 to 50 mmol/l phosphate buffer. Of course, combinations of these buffer systems are also part of the present invention. The pH value may be adjusted with a corresponding base, e.g. NaOH in the phosphate buffer system and a corresponding acid, e.g. sulfuric acid in the arginine buffer system, respectively.

The buffer and the anion should be present in the solution in accordance with this invention to maintain a pH in the range of 5.5 to about 7. Any amount of anion and buffer can be utilized in accordance with this invention so long as the pH is maintained at this level.

If desired, pharmaceutical compositions of this invention may contain conventional pharmaceutically acceptable excipients. These excipients can be utilized to improve the properties of these compositions in accordance with conventional procedures. On the other hand, these excipients need not be present and the injectable and/or intravenous solutions of this invention can be prepared without these excipients. In accordance with the preferred embodiment of this invention, the compositions may comprise one or more pharmaceutically acceptable excipients. These pharmaceutically acceptable excipient may be selected from pharmaceutically acceptable salts, diluents and/or solvents and/or preservatives, etc., e.g. tonicity agents (isotonic-making agents), polyols, anti-oxidants or non-ionic detergents. Examples for these substances are sodium chloride, calcium chloride, sorbitol, mannitol, glycerol, saccharose, trehalose, acetylcysteine, polysorbate 20, polysorbate 80, or pluronic F68.

In a preferred embodiment of the present invention the pharmaceutical compositions may contain a polyol selected from the group consisting of mannitol, sorbitol, glycerol, trehalose and saccharose, preferably mannitol. The concentration of the polyol can vary between 1 and 10% (w/v). The term w/v as used herein is the weight of the additive as a percent based upon the total volume of the aqueous composition of this invention.

Examples for anti-oxidants are cysteine, methionine, acetylcysteine or ascorbic acid, preferably methionine. Antioxidants may usually be added in a concentration between 0.01 and 0.5% (w/v) or, e.g. in the case of methionine in a concentration of 1–20 mM based upon the composition of this invention as an aqueous liquid solution.

Also, the above described compositions can optionally comprise an isotonic-making agent of from about 0.01 to about 0.9% w/w. These compounds are known in the art; examples for these agents are sodium chloride or sodium sulfate. In a preferred embodiment of the present invention the compositions are isotonic solutions. The above composition may also contain a non-ionic detergent like polysorbate 20, polysorbate 80 or pluronic F 68, preferably pluronic F 68, e.g. up to 1% (w/v), more preferably up to 0.1% (w/v), e.g. 0.001% to 0.01% (w/v).

In accordance with another embodiment, the above composition may also contain additional salts, e.g. from 0.1 to 1 mmol/l $CaCl_2$ when such salt is present.

The present invention is especially useful for the preparation of pharmaceutical compositions comprising erythropoietin as pharmaceutically active ingredient. The term "erythropoietin" or "erythropoietin protein" or "EPO" is as follows: particularly the terms refer to a glycoprotein, e.g. the human erythropoietin, e.g. having the amino acid sequence set out in (SEQ ID NO: 1) or (SEQ ID NO: 2) or an amino acid sequence substantially homologous thereto, whose biological properties relate to the stimulation of red blood cell production and the stimulation of the division and differentiation of committed erythroid progenitors in the bone marrow. As used herein, these terms include such proteins modified deliberately, as for example, by site directed mutagenesis or accidentally through mutations. These terms also include modifications of the above sequences where these sequences have been modified by having from 1 to 6 additional sites for glycosylation, or modified by having at least one additional amino acid at the carboxy terminal end of the glycoprotein, wherein the additional amino acid includes at least one glycosylation site, and modificatins of the above sequences where these sequences have been modified by having an amino acid sequence which includes a rearrangement of at least one site for glycosylation. These terms include both natural and recombinantly produced human erythropoietin.

As set out in detail below, the preparation and purification of EPO are well known in the art. By an erythropoietin product is meant the natural or recombinant protein product, preferably human, as obtained from any conventional source such as tissues, protein synthesis, cell culture with natural or recombinant cells or as modified as described herein. Any glycosylated protein product having the activity of erythropoietin such as having the in vivo biological activity of causing bone marrow cells to increase production of reticulocytes and red blood cells, such as muteins or otherwise modified proteins, is encompassed. Recombinant EPO may be prepared via expression in CHO—, BHK— or HeLa cell lines, by recombinant DNA technology or by endogenous gene activation. Expression of proteins, including, by endogenous gene activation, is well known in the art and is disclosed, for example in U.S. Pat. Nos. 5,733,761, 5,641,670, and 5,733,746, and international patent publication Nos. WO 93/09222, WO 94/12650, WO 95/31560, WO 90/11354, WO 91/06667 and WO 91/09955, the contents of each of which are incorporated herein by reference. The preferred EPO species for the preparation of erythropoietin glycoprotein products are human EPO species. More preferably, the EPO species is the human EPO having the amino acid sequence set out in SEQ ID NO: 1 or SEQ ID NO: 2, more preferably the amino acid sequence SEQ ID NO: 1.

Further, the erythropoietin product of this invention may be a glycoprotein of the above sequences modified by having from 1 to 6 additional sites for glycosylation. Glycosylation of a protein, with one or more oligosaccharide groups, occurs at specific locations along a polypeptide backbone and greatly affects the physical properties of the protein such as protein stability, secretion, subcellular localization, and biological activity. Glycosylation is usually of two types. O-linked oligosaccharides are attached to serine or threonine residues and N-linked oligosaccharides are attached to asparagine residues. One type of oligosaccharide found on both N-linked and O-linked oligosaccharides is N-acetylneuraminic acid (sialic acid), which is a family of amino sugars containing 9 or more carbon atoms. Sialic acid is usually the terminal residue on both N-linked and O-linked oligosaccharides and, because it bears a negative charge, confers acidic properties to the glycoprotein. Human erythropoietin, having 165 amino acids, contains three N-linked and one O-linked oligosaccharide chains which comprise about 40% of the total molecular weight of the glycoprotein. N-linked glycosylation occurs at asparagine residues located at positions 24, 38, and 83 and O-linked glycosylation occurs at a serine residue located at position 126. The oligosaccharide chains are modified with terminal sialic acid residues. Enzymatic removal of all sialic acid residues from the glycosylated erythropoietin results in loss of in vivo activity but not in vitro activity because sialylation of erythropoietin prevents its binding, and subsequent clearance, by hepatic binding protein.

The term "erythropoietin product" of the present pharmaceutical composition includes such modifications of human erythropoietin that have one or more changes in the amino acid sequence of human erythropoietin which result in an increase in the number of sites for sialic acid attachment. These glycoprotein modifications may be generated by site-directed mutagenesis having additions, deletions, or substitutions of amino acid residues that increase or alter sites that are available for glycosylation. Glycoprotein analogs having levels of sialic acid greater than those found in human erythropoietin are generated by adding glycosylation sites which do not perturb the secondary or tertiary conformation required for biological activity. The erythropoietin glycoproteins products of the present invention also include such modifications of the human erythropoietin sequences which have increased levels of carbohydrate attachment at a glycosylation site which usually involve the substitution of one or more amino acids in close proximity to an N-linked or O-linked site. The glycoprotein products of the compositions of the present invention also include modifications of said sequences having one or more amino acids extending from the carboxy terminal end of erythropoietin and providing at least one additional carbohydrate site. The erythropoietin protein products of the present composition also include modifications of said sequences having an amino acid sequence which includes a rearrangement of at least one site for glycosylation. Such a rearrangement of glycosylation site involves the deletion of one or more glycosylation sites in human erythropoietin and the addition of one or more non-naturally occurring glycosylation sites. Increasing the number of carbohydrate chains on erythropoietin, and therefore the number of sialic acids per erythropoietin molecules may confer advantageous properties such as increased solubility, greater resistance to proteolysis, reduced immunogenecity, increased serum half-life, and increased biological activity. Such erythropoietins having additional glycosylation sites are disclosed in more detail in European Patent Application 640 619, to Elliot published Mar. 1, 1995.

In a preferred embodiment, the pharmaceutical composition of the present invention comprises erythropoietin proteins products having the above amino acid sequence modified by including at least one additional site for glycosylation such as, but not limited to, erythropoietins comprising the sequence of human erythropoietin modified by a modification selected from the following:

$Asn^{30}Thr^{32}$;

$Asn^{51}Thr^{53}$,

Asn$^{57}$Thr$^{59}$;
Asn$^{69}$;
Asn$^{69}$Thr$^{71}$;
Ser$^{68}$Asn$^{69}$Thr$^{7}$;
Val$^{87}$Asn$^{88}$Thr$^{90}$;
Ser$^{87}$Asn$^{88}$Thr$^{90}$;
Ser$^{87}$Asn$^{88}$Gly$^{89}$Thr$^{90}$;
Ser$^{87}$Asn$^{88}$Thr$^{90}$Thr$^{92}$;
Ser$^{87}$Asn$^{88}$Thr$^{90}$Ala$^{162}$;
Asn$^{69}$Thr$^{71}$Ser$^{87}$Asn$^{88}$Thr$^{90}$;
Asn$^{30}$Thr$^{32}$Val$^{87}$Asn$^{88}$Thr$^{90}$;
Asn$^{89}$Ile$^{90}$Thr$^{91}$;
Ser$^{87}$Asn$^{89}$Ile$^{90}$Thr$^{91}$;
Asn$^{136}$Thr$^{138}$;
Asn$^{138}$Thr$^{140}$;
Thr$^{125}$; and
Pro$^{124}$Thr$^{125}$.

The notation used herein for modification of amino acid sequence means that the position(s) of the corresponding unmodified protein (e.g. hEPO of SEQ ID NO:1 or SEQ ID NO:2) indicated by the superscripted number(s) is changed to the amino acid(s) that immediately precede the respective superscripted number(s).

The erythropoietin protein product may also have at least one additional amino acid at the carboxy terminal end of the glycoprotein, wherein the additional amino acid includes at least one glycosylation site. The additional amino acid may comprise a peptide fragment derived from the carboxy terminal end of human chorionic gonadotropin. Preferably, the glycoprotein is an analog selected from the group consisting of (a) human erythropoietin having the amino acid sequence, Ser Ser Ser Ser Lys Ala Pro Pro Pro Ser Leu Pro Ser Pro Ser Arg Leu Pro Gly Pro Ser Asp Thr Pro Ile Leu Pro Gln (SEQ ID NO:3), extending from the carboxy terminus; (b) the analog in (a) further comprising Ser$^{87}$ Asn$^{88}$ Thr$^{90}$ EPO; and (c) the analog in (a) further comprising Asn$^{30}$ Thr$^{32}$ Val$^{87}$ Asn$^{88}$ Thr$^{90}$ EPO.

The erythropoietin protein product may also have an amino acid sequence which includes a rearrangement of at least one site for glycosylation. The rearrangement may comprise a deletion of any of the N-linked carbohydrate sites in the sequence of human erythropoietin and an addition of an N-linked carbohydrate site at position 88 of the amino acid sequence of human erythropoietin. Preferably, the glycoprotein is an analog selected from the group consisting of Gln$^{24}$ Ser$^{87}$ Asn$^{88}$ Thr$^{90}$ EPO; Gln$^{38}$ Ser$^{87}$ Asn$^{88}$ Thr$^{90}$ EPO; and Gln$^{83}$ Ser$^{87}$ Asn$^{88}$ Thr$^{90}$ EPO.

More particularly, the erythropoietin glycoprotein product of the present pharmaceutical composition as described above may also include pegylated derivatives thereof. Pegylated derivatives of erythropoietin and their preparation are known in the art and described for example in EP-A-539, 167, EP-A-605,963, WO 93/25212, WO 94/20069, WO 95/11924, U.S. Pat. No. 5,56, EP-A-584,876, WO 92/16555, WO 94/28024, WO 97/04796, U.S. Pat. Nos. 5,359,030 and 5,681,811, U.S. Pat. No. 4,179,337, Japanese Patent, WO 98/32466, U.S. Pat. No. 5,324,650. A preferred embodiment of pegylated erythropoietin species refer to the derivatives as described below.

Accordingly, the present invention also refers to an erythropoietin conjugate, said conjugate comprising an erythropoietin protein as described above having at least one free amino group and having the in vivo biological activity of causing bone marrow cells to increase production of reticulocytes and red blood cells and selected from the group consisting of human erythropoietin and analogs thereof which have sequence of human erythropoietin modified by the addition of from 1 to 6 glycosylation sites or a rearrangement of at least one glycosylation site; said erythropoietin being covalently linked to [poly(ethylene glycol)] with a linker of the formula —CO—(CH$_2$)$_x$—(OCH$_2$CH$_2$)$_m$—OR with the —CO (i.e. carbonyl) of each poly (ethylene glycol) group forming an amide bond with one of said amino groups; wherein R is lower alkyl; x is 2 or 3; m is from about 450 to about 900; n is from 1 to 3; and n and m are chosen so that the molecular weight of the conjugate minus the erythropoietin glycoprotein is from 20 kilodaltons to 100 kilodaltons. This invention further provides pharmaceutical compositions containing conjugates described herein in which the percentage of conjugates in which n is 1 is at least ninety percent, preferably at least ninety-two percent, ore preferably ninety-sex percent of all conjugates of the composition.

More specifically the above pegylated conjugates may be represented by formula (I)

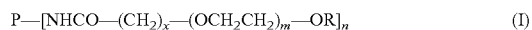

$$P\text{—}[NHCO\text{—}(CH_2)_x\text{—}(OCH_2CH_2)_m\text{—}OR]_n \qquad (I)$$

wherein P is the residue of an erythropoietin protein as described herein, (i.e. without the amino group or amino groups which form an amide linkage with the carbonyl shown in Formula I), having the in vivo biological activity of causing bone marrow cells to increase production of reticulocytes and red blood cells; and wherein R is lower alkyl; x is 2 or 3; m is from about 450 to about 900; n is from 1 to 3; and n and m are chosen so that the molecular weight of the conjugate minus the erythropoietin glycoprotein is from 20 kilodaltons to 100 kilodaltons.

As used herein, "lower alkyl" means a linear or branched alkyl group having from one to six carbon atoms. Examples of lower alkyl groups include methyl, ethyl and isopropyl. In accordance with this invention, R is any lower alkyl. Conjugates in which R is methyl are preferred.

The symbol "m" represents the number of ethylene oxide residues (OCH$_2$CH$_2$) in the poly(ethylene oxide) group. A single PEG (polyethylene glycol) subunit of ethylene oxide has a molecular weight of about 44 daltons. Thus, the molecular weight of the conjugate (excluding the molecular weight of the EPO) depends on the number "m". In the conjugates of this invention "m" is from about 450 to about 900 (corresponding to a molecular weight of about 20 kDa to about 40 kDa), preferably from about 650 to about 750 (corresponding to a molecular weight of about 30 kDa). The number m is selected such that the resulting conjugate of this invention has a physiological activity comparable to unmodified EPO, which activity may represent the same as, more than, or a fraction of the corresponding activity of unmodified EPO. A molecular weight of "about" a certain number means that it is within a reasonable range of that number as determined by conventional analytical techniques. The number "m" is selected so that the molecular weight of each poly(ethylene glycol) group covalently linked to the erythropoietin glycoprotein is from about 20 kDa to about 40 kDa, and is preferably about 30 kDa.

In the conjugates of this invention, the number "n" is the number of poly(ethylene glycol) groups covalently bound to free amino groups (including ε-amino groups of a lysine amino acid and/or the amino-terminal amino group) of an erythropoietin protein via amide linkage(s). A conjugate of this invention may have one, two, or three PEG groups per molecule of EPO. "n" is an integer ranging from 1 to 3, preferably "n" is 1 or 2, and more preferably "n" is 1. A preferred conjugate of the conjugates described above comprises compounds wherein x is 2, m is 650 to 750, n is 1 and R is methyl.

The compound of formula (I) can be prepared from the known polymeric material:

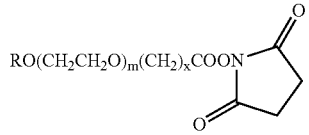
(II)

in which R and m are as described above, by condensing the compound of Formula II with the erythropoietin glycoprotein. Compounds of formula (II) in which x is 3 are alpha-lower alkoxy, butyric acid succinimidyl esters of poly(ethylene glycol) (lower alkoxy-PEG-SBA). Compounds of formula (II) in which x is 2 are alpha-lower alkoxy, propionic acid succinimidyl esters of poly(ethylene glycol) (lower alkoxy-PEG-SPA). Any conventional method of reacting an activated ester with an amine to form an amide can be utilized. In the reaction described above, the exemplified succinimidyl ester is a leaving group causing the amide formation. The use of succinimidyl esters such as the compounds of formula II to produce conjugates with proteins are disclosed in U.S. Pat. No. 5,672,662, issued Sep. 30, 1997 (Harris, et al.).

Human EPO contains nine free amino groups, the amino-terminal amino group plus the ε-amino groups of 8 lysine residues. When the pegylation reagent was combined with a SBA compound of Formula II, it has been found that at pH 7.5, a protein:PEG ratio of 1:3, and a reaction temperature of from 20–25° C., a mixture of mono-, di-, and trace amounts of the tri-pegylated species were produced. When the pegylation reagent was a SPA compound of Formula II, at similar conditions except that the protein:PEG ratio was 1:2, primarily the mono-pegylated species is produced. The pegylated EPO can be administered as a mixture, or as the cation exchange chromatography separated different pegylated species. By manipulating the reaction conditions (e.g., ratio of reagents, pH, temperature, protein concentration, time of reaction etc.), the relative amounts of the different pegylated species can be varied.

The pharmaceutical compositions as described above may also contain an erythropoietin protein as defined above having at least one free amino group and having the in vivo biological activity of causing bone marrow cells to increase production of reticulocytes and red blood cells and selected from the group consisting of human erythropoietin and analogs thereof which have the primary structure of human erythropoietin modified by the addition of from 1 to 6 glycosylation sites; said glycoprotein being covalently linked to from one to three lower-alkoxy poly(ethylene glycol) groups, each poly(ethylene glycol) group being covalently linked to the glycoprotein via a linker of the formula —C(O)—X—S—Y— with the C(O) of the linker forming an amide bond with one of said amino groups, X is—$(CH_2)_k$— or —$CH_2(O-CH_2-CH_2)_k$—, k is from 1 to 10, Y is

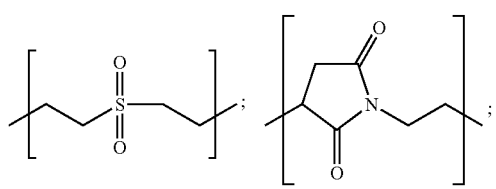

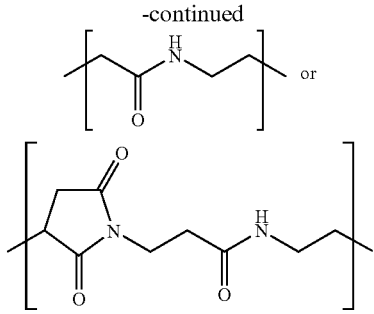

the average molecular weight of each poly(ethylene glycol) moiety is from about 20 kilodaltons to about 40 kilodaltons, and the molecular weight of the conjugate is from about 51 kilodaltons to about 175 kilodaltons.

This erythropoietin species may also be represented by formula (III)

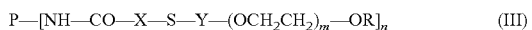
(III)

wherein R may be any lower alkyl, by which is meant a linear or branched alkyl group having from one to six carbon atoms such as methyl, ethyl, isopropyl, etc. A preferred alkyl is methyl. X may be —$(CH_2)_k$— or —$CH_2(O-CH_2-CH_2)_k$—, wherein k is from 1 to about 10. Preferably, k is from 1 to about 4, more preferably, k is 1 or 2. Most preferably, X is —$(CH_2)$.

In Formula 1, Y is preferably

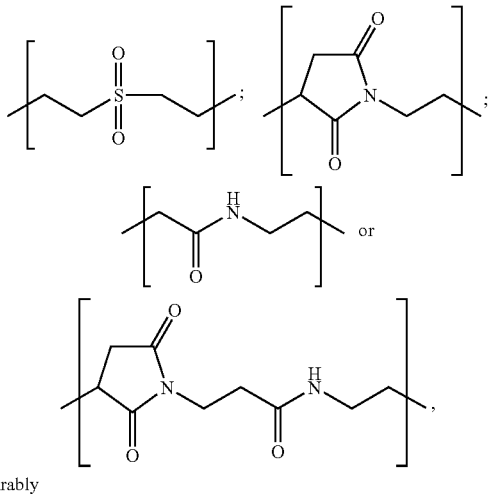

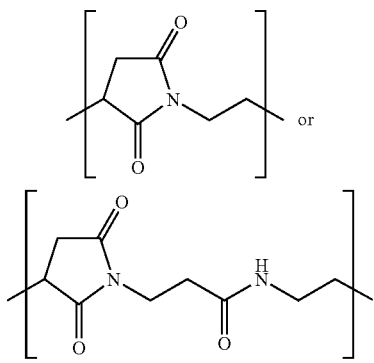

more preferably

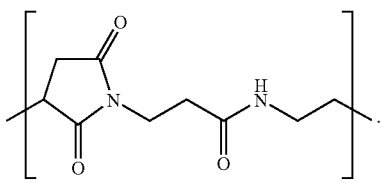

In formula (III), the number m is selected such that the resulting conjugate of formula (III) has a physiological activity comparable to unmodified EPO, which activity may represent the same as, more than, or a fraction of the corresponding activity of unmodified EPO. m represents the number of ethylene oxide residues in the PEG unit. A single PEG subunit of $-(OCH_2CH_2)-$ has a molecular weight of about 44 daltons. Thus, the molecular weight of the conjugate (excluding the molecular weight of the EPO) depends on the number m. A molecular weight of "about" a certain number means that it is within a reasonable range of that number as determined by conventional analytical techniques. m is an integer ranging from about 450 to about 900 (corresponding to a molecular weight of from 20 to 40 kDa), preferably m is from about 550 to about 800 (about 24 to 35 kDa), and most preferably m is from about 650 to about 700 (about 29 to about 31 kDa).

In formula (III), the number n is the number of ε-amino groups of a lysine amino acid in an erythropoietin protein covalently bound to a PEG unit via an amide linkage. A conjugate of this invention may have one, two, or three PEG units per molecule of EPO. n is an integer ranging from 1 to 3, preferably n is 1 or 2, and more preferably n is 1.

Preferred erythropoietin proteins of formula (III) are represented by the formulae:

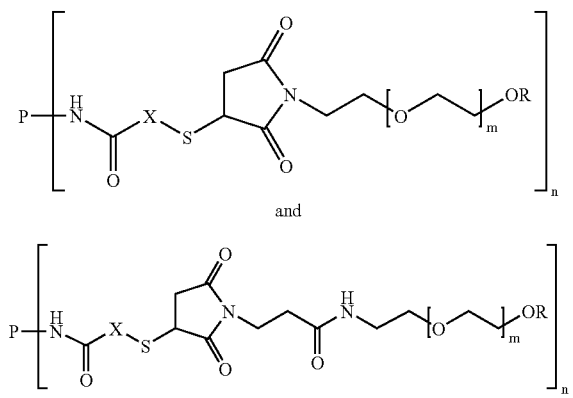

Most preferred erythropoietin glycoprotein products are represented by the formula:

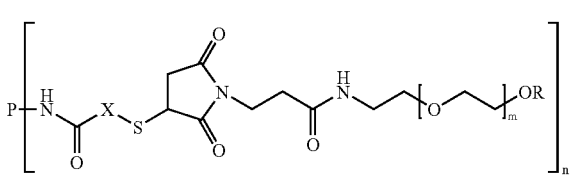

wherein in the above formulae n is an integer from 1 to 3; m is an integer from 450 to 900; R is lower alkyl; X is $-(CH_2)_k-$ or $-CH_2(O-CH_2-CH_2)_k-$, and P is the residue of the erythropoietin glycoprotein without the amino group or groups which form an amide linkage with X.

Other preferred erythropoietin glycoprotein products are represented by the formulae:

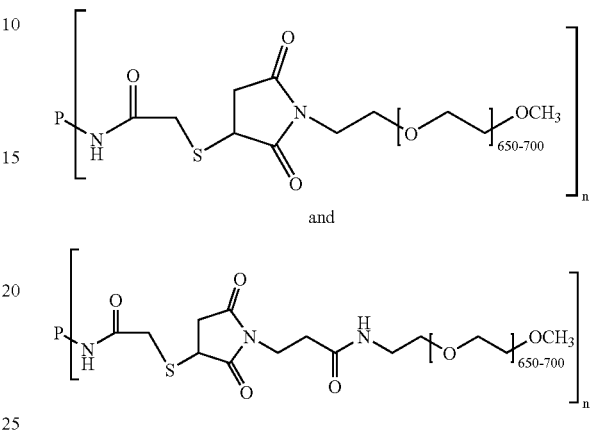

and

More preferred erythropoietin glycoprotein products are represented by the formula:

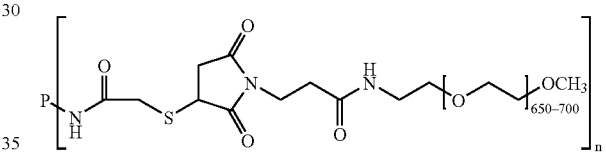

These erythropoietin proteins may be prepared by (a) covalently reacting an ε-amino group of a lysine amino acid of an erythropoietin protein represented by the formula, $P-[NH_2]_n$, with a bi-functional reagent represented by the formula, Z—CO—X—S—Q, to form an intermediate with an amide linkage represented by the formula:

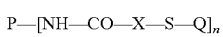

P—[NH—CO—X—S—Q]$_n$ wherein P is an erythropoietin protein less the amino group which forms an amide linkage; n is an integer ranging from 1 to 3; Z is a reactive group, e.g. a carboxylic-NHS ester; X is $-(CH_2)_k-$ or $-CH_2(O-CH_2-CH_2)_k-$, wherein k is from 1 to about 10; and Q is a protecting group, like alkanoyl, e.g. acetyl.

(b) covalently reacting the intermediate with an amide linkage from step (a) with an activated poly(ethylene glycol) derivative represented by the formula, $W-[OCH_2CH_2]_m-$OR, to form an erythropoietin glycoprotein product represented by the formula:

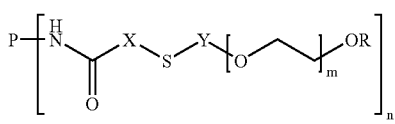

wherein W is a sulfhydryl reactive form of Y; m is an integer ranging from about 450 to about 900; R is lower alkyl; and Y is as defined above.

In this embodiment, the bi-functional reagent is preferably N-succinimidyl-S-acetylthiopropionate or N-succinimidyl-S-acetylthioacetate, Z is preferably N-hydroxy-succinimide, and the activated poly(ethylene glycol) derivative W—[OCH$_2$CH$_2$]$_m$—OR is preferably selected from the group consisting of iodo-acetyl-methoxy-PEG, methoxy-PEG-vinylsulfone, and methoxy-PEG-maleimide.

In more detail, the erythropoietin proteins of formula (III) maybe prepared by covalent linking of thiol groups to EPO ("activation") and coupling the resulting activated EPO with a poly(ethylene glycol) (PEG) derivative. The first step for the preparation of pegylated EPO according to the present invention comprises covalent linking of thiol groups via NH$_2$-groups of EPO. This activation of EPO is performed with bi-functional reagents which carry a protected thiol group and an additional reactive group, such as active esters (e.g., a succinimidylester), anhydrides, esters of sulphonic acids, halogenides of carboxylic acids and sulphonic acids, respectively. The thiol group is protected by groups known in the art, e.g., acetyl groups. These bi-functional reagents are able to react with the ε-amino groups of the lysine amino acids by forming an amide linkage. The first step of the reaction is set out below:

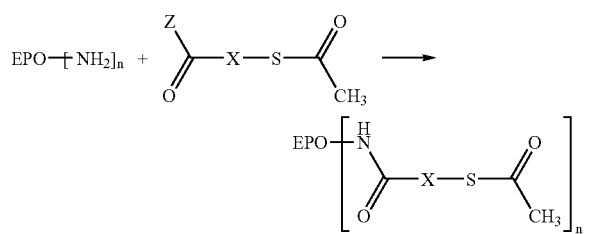

EPO, n and X are as defined above and Z is a reactive group known in the art, e.g. a N-hydroxy-succinimide (NHS) substituent of the formula

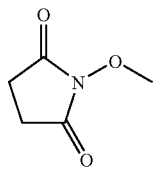

In a preferred embodiment the activation of the ε-amino lysine groups is performed by reaction with bi-functional reagents having a succinimidyl moiety. The bi-functional reagents may carry different spacer species, e.g. —(CH$_2$)$_k$— or —CH$_2$—(O—CH$_2$—CH$_2$—)$_k$— moieties, wherein k is from 1 to about 10, preferably from 1 to about 4, and more preferably 1 or 2, and most preferably 1. Examples of these reagents are N-succinimidyl-S-acetylthiopropionate (SATP) and N-succinimidyl-S-acetylthioacetate (SATA)

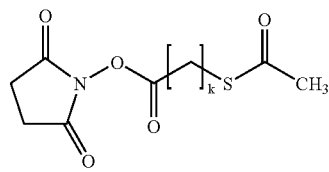

Acetylthioalkyl-carboxylic-NHS-ester, like

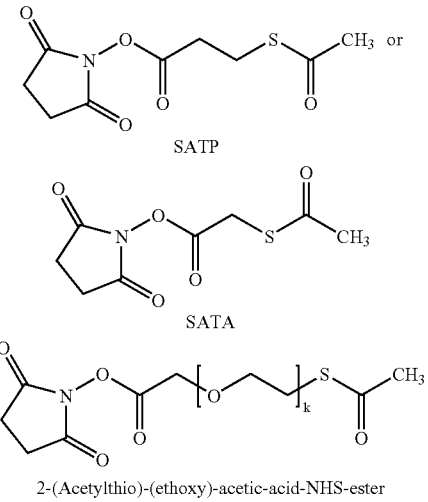

2-(Acetylthio)-(ethoxy)-acetic-acid-NHS-ester with k as defined above.

The preparation of the bi-functional reagents is known in the art. Precursors of 2-(acetylthio)-(ethoxy)$_k$-acetic-acid-NHS-esters are described in DE-3924705, while the derivatization to the acetylthio compound is described by March, J., Advanced Organic Chemistry, McGraw-Hill, 1977, 375–376. SATA is commercially available (Molecular Probes, Eugene, OR, USA and Pierce, Rockford, Ill.).

The number of thiol groups to be added to an EPO molecule can be selected by adjusting the reaction parameters, i.e., the protein (EPO) concentration and the protein/bi-functional reagent ratio. Preferably, the EPO is activated by covalently linking from 1 to 5 thiol groups per EPO molecule, more preferably from 1.5 to 3 thiol groups per EPO molecule. These ranges refer to the statistical distribution of the thiol group over the EPO protein population.

The reaction is carried out, for example, in an aqueous buffer solution, pH 6.5–8.0, e.g., in 10 mM potassium phosphate, 50 mM NaCl, pH 7.3. The bi-functional reagent may be added in DMSO. After completion of the reaction, preferably after 30 minutes, the reaction is stopped by addition of lysine. Excess bifunctional reagent may be separated by methods known in the art, e.g., by dialysis or column filtration. The average number of thiol groups added to EPO can be determined by photometric methods described in, for example, Grasetti, D. R. and Murray, J. F. in J. Appl. Biochem. Biotechnol. 119, 41–49 (1967).

The above reaction is followed by covalent coupling of an activated poly(ethylene glycol) (PEG) derivative. Suitable PEG derivatives are activated PEG molecules with an average molecular weight of from about 20 to about 40 kDa, more preferably from about 24 to about 35 kDa, and most preferably about 30 kDa.

Activated PEG derivatives are known in the art and are described in, for example, Morpurgo, M. et al. J. Bioconj. Chem. (1996) 7, page 363 ff for PEG-vinylsulfone. Linear chain and branched chain PEG species are suitable for the preparation of the compounds of Formula 1. Examples of reactive PEG reagents are iodo-acetyl-methoxy-PEG and methoxy-PEG-vinylsulfone:

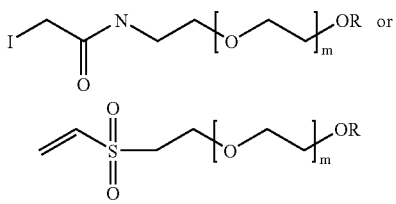

The use of these iodo-activated substances is known in the art and described e.g. by Hermanson, G. T. in Bioconjugate Techniques, Academic Press, San Diego (1996) p. 147–148.

Most preferably, the PEG species are activated by maleimide using (alkoxy-PEG-maleimide), such as methoxy-PEG-maleimide (MW 30000; Shearwater Polymers, Inc.). The structure of alkoxy-PEG-maleimide is as follows:

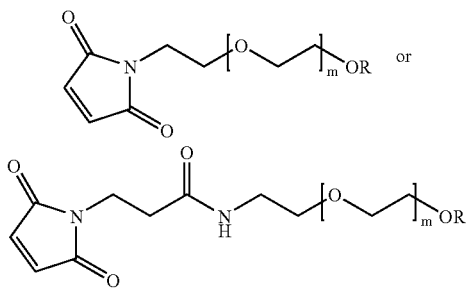

with R and m are as defined above, preferably

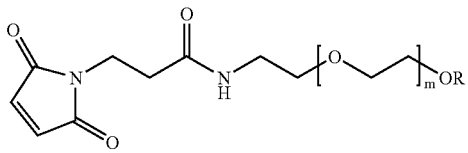

The coupling reaction with alkoxy-PEG-maleimide takes place after in situ cleavage of the thiol protecting group in an aqueous buffer solution, e.g. 10 mM potassium phosphate, 50 mM NaCl, 2 mM EDTA, pH 6.2. The cleavage of the protecting group may be performed, for example, with hydroxylamine in DMSO at 25° C., pH 6.2 for about 90 minutes. For the PEG modification the molar ratio of activated EPO/alkoxy-PEG-maleimide should be from about 1:3 to about 1:6, and preferably 1:4. The reaction may be stopped by addition of cysteine and reaction of the remaining thiol (—SH) groups with N-methylmaleimide or other appropriate compounds capable of forming disulfide bonds. Because of the reaction of any remaining active thiol groups with a protecting group such as N-methylmaleimide or other suitable protecting group, the EPO glycoproteins in the conjugates of this invention may contain such protecting groups. Generally the procedure described herein will produce a mixture of molecules having varying numbers of thiols protected by different numbers of the protecting group, depending on the number of activated thiol groups on the glycoprotein that were not conjugated to PEG-maleimide.

Whereas N-methylmaleimide forms the same type of covalent bond when used to block the remaining thiol-groups on the pegylated protein, disulfide compounds will lead in an intermolecular sulfide/disulfide exchange reaction to a disulfide bridged coupling of the blocking reagent. Preferred blocking reagents for that type of blocking reaction are oxidized glutathione (GSSG), cysteine and cystamine. Whereas with cysteine no additional net charge is introduced into the pegylated protein, the use of the blocking reagents GSSG or cystamine results in an additional negative or positive charge.

The further purification of the compounds of formula (III), including the separation of mono-, di- and tri-pegylated EPO species, may be done by methods known in the art, e.g., column chromatography.

A composition comprising pegylated erythropoietin derivatives preferably contains at least ninety percent mono-PEG conjugates, i.e. in which n is 1, can be prepared as shown in Example 5. Usually mono-PEG conjugates of erythropoietin glycoproteins are desirable because they tend to have higher activity than di-PEG conjugates. The percentage of mono-PEG conjugates as well as the ratio of mono- and di-PEG species can be controlled by pooling broader fractions around the elution peak to decrease the percentage of mono-PEG or narrower fractions to increase the percentage of mono-PEG in the composition. About ninety percent mono-PEG conjugates is a good balance of yield and activity. Sometimes compositions in which, for example, at least ninety-two percent or at least ninety-six percent of the conjugates are mono-PEG species (n equals 1) may be desired. In an embodiment of this invention the percentage of conjugates where n is 1 is from ninety percent to ninety-six percent.

Compositions according to the present inventions may comprise 10 to 10000 μg of an erythropoietin protein per ml as defined above. Preferably, the compositions comprise 10 to 1000 μg, e.g. 10, 50, 100 or 400 μg per ml.

Further, the compositions according to the present invention may comprise 10 μg to 10000 μg erythropoietin protein per ml, 10–200 mmol/l sulfate, 10 to 50 mmol/l phosphate, pH 6.0 to 6.5. This composition may also comprise up to 20 mM methionine, 1–5% of a polyol (w/v), up to 0.1% pluronic F68 (w/v) and optionally up to 1 mM CaCl$_2$. An example of this composition comprises 10 μg to 10000 μg erythropoietin protein per ml, 40 mmol/l sulfate, 10 mmol/l phosphate, 3% mannitol (w/v), 10 mM methionine, 0.01% pluronic F68 (w/v), pH 6.2.

In a further embodiment of the present invention, the composition may comprise 10 μg to 10000 μg erythropoietin protein per ml, 10 to 100 mmol/l NaCl, 10 to 50 mmol/l phosphate pH 6.0 to 7.0, optionally 1–5% (w/v) of a polyol. Further, this composition may comprise up to 20 mM methionine, up to 0.1% pluronic F68 (w/v) and optionally 7.5 mmol/l CaCl$_2$. Specifically, this composition may comprise 10 μg to 10000 μg erythropoietin protein per ml, 100 mmol/l NaCl, 10 mM methionine, 0.01% pluronic F68 (w/v), and 10 mmol/l phosphate, pH 7.0.

The present invention also refers to the above composition comprising 10 μg to 10000 μg erythropoietin protein per ml, 10 to 50 mmol/l arginine, pH 6 to pH 6.5, 10 to 100 mmol/l sodium sulfate. In addition, this composition may comprise up to 20 mM methionine, up to 0.1% pluronic F68 (w/v), optionally up to 1 mmol/l CaCl$_2$ and optionally 1–5% (w/v) of a polyol. Specifically, this composition may 10 μg to 10000 μg erythropoietin protein per ml, 40 mmol/l arginine, pH 6.2, 30 mmol/l sodium sulfate, 3% mannitol (w/v), 10 mM methionine, 0.01% pluronic F68 (w/v) and optionally 1 mmol/l CaCl$_2$.

A preferred embodiment of the present invention refers to compositions comprising 10 to 10000 µg/ml erythropoietin, preferably 25 to 2,500 µg/ml erythropoietin, and
a) 10 mM sodium/potassium phosphate, 100 mM NaCl, pH 7.0 or
b) 10 mM sodium phosphate, 120 mM sodium sulfate, pH 6.2 or
c) 10 mM sodium phosphate, 40 mM sodium sulfate, 3% mannitol (w/v), pH 6.2 or
d) 10 mM sodium phosphate, 40 mM sodium sulfate, 3% mannitol (w/v), 10 mM methionine, 0.01% pluronic F68 (w/v), pH 6.2 or
e) 40 mM arginine, 30 mM sodium sulfate, 3% mannitol (w/v), pH 6.2 or
f) 40 mM arginine, 30 mM sodium sulfate, 3% mannitol (w/v), 10 mM methionine, 0.01% pluronic F68 (w/v), pH 6.2.

In the most preferred embodiment, the compositions comprise an amount erythropoietin protein of 50, 100, 400, 800 or 2,500 µg/ml. The most preferred compositions comprise either 10 mM sodium phosphate, 40 mM sodium sulfate, 3% mannitol (w/v), 10 mM methionine, 0.01% pluronic F68 (w/v), pH 6.2 or 40 mM arginine, 30 mM sodium sulfate, 3% mannitol (w/v), 10 mM methionine, 0.01% pluronic F68 (w/v), pH 6.2.

The compositions of the present invention may be in the form of a spray-dried powder.

Further the invention relates to a composition which is a lyophilisate or a spray-dried powder of the aqueous liquid solution as described above. The lyophilisate or spray-dried composition may be re-constituted to form a liquid solution by the addition of a solvent, e.g. water, or applied directly by e.g. an inhalation device or a transdermal application device. Upon addition of water to reconstitute this lyophilisate or a spray-dried powder, there is formed a liquid pharmaceutical composition as an aqueous solution comprising the erythropoietin glycoprotein product, a multiple charged inorganic anion, a pharmaceutically acceptable buffer, said anion and said buffer being present in said solution in an amount to provide the solution with a pH of from 5.5 to about 7.0 and said product being present in said solution in a sufficient amount to provide a therapeutically effective amount of said product when the solution or a portion of said solution is administered to a patient. In accordance with a preferred embodiment, upon reconstituion of this lyophilisate or a spray-dried powder with water, there is formed a liquid pharmaceutical composition in the form of an aqueous solution comprising from 10 µg to 10,000 µg per ml of said solution of an erythropoietin glycoprotein product, from 10 to 200 mmol per liter of said solution of a multiple charged inorganic anion and from 10 to 50 mmol per liter of said solution of a pharmaceutically acceptable buffer, said anion and said buffer being present in said solution in an amount to provide the solution with a pH of from 5.5 to about 7.0.

The invention also comprises a process for preparing a composition as described above, comprising mixing a erythropoietin protein with a solution comprising a multiple, negatively charged anion and optionally one or more pharmaceutically acceptable excipients as defined above.

In addition, the present invention refers to the use of a composition as defined above for the preparation of medicaments useful for the treatment and prevention of diseases correlated with anemia in chronic renal failure patients (CRF), AIDS and/or for the treatment of cancer patients undergoing chemotherapy. This includes a method for the treatment and prevention of diseases involving anemia in chronic renal failure patients (CRF), AIDS and cancer patients undergoing chemotherapy comprising the step of administering to a patient a composition as defined above.

A further embodiment of the present invention refers to devices for local and systemic sustained release comprising a composition as defined above. This could be any kind of implant that provides a controlled release of erythropoietin comprising the composition described above, like e.g. polymer-based micro- or nanoparticles. The composition described above can also be provided as a pre-filled syringe or in any other application device, like e.g. a needle-free injection device or an inhalation device.

The preparation of erythropoietin as ingredient for the compositions as described above or as starting point for the preparation of erythropoietin derivatives as described above is described in detail for example in U.S. Pat. Nos. 5,547,933 and 5,621,080, EP-B 0 148 605, Huang, S. L., Proc. Natl. Acad. Sci. USA (1984) 2708–2712, EP-B 0 205 564, EP-B 0 209 539 and EP-B 0 411 678 as well as Lai, P. H. et al., J. Biol. Chem. 261 (1986) 3116–3121, an Sasaki, H. et al., J. Biol. Chem. 262 (1987) 12059–12076. Erythropoietin for therapeutic uses maybe produced by recombinant means (EP-B 0 148 605, EP-B 0 209 539 and Egrie, J. C., Strickland, T. W., Lane, J. et al. (1986) Immunobiol. 72: 213–224).

Methods for the expression and preparation of erythropoietin in serum free medium are described for example in WO 96/35718, to Burg published 14 Nov. 1996, and in European Patent Publication No. 513 738, to Koch published 12 Jun. 1992. In addition to the publications mentioned above, it is known that a serum-free fermentation of recombinant CHO cells which contain an EPO gene can be carried out. Such methods are described for example in EP-A 0 513 738, EP-A 0 267 678 and in a general form by Kawamoto, T. et al., Analytical Biochem. 130 (1983) 445–453, EP-A 0 248 656, Kowar, J. and Franek, F., Methods in Enzymology 421 (1986) 277–292, Bavister, B., Expcology 271 (1981) 45–51, EP-A 0 481 791, EP-A 0 307 247, EP-A 0 343 635, WO 88/00967.

In EP-A 0 267 678 an ion exchange chromatography on S-Sepharose, a preparative reverse phase HPLC on a $C_8$ column and a gel filtration chromatography are described for the purification of EPO produced in serum-free culture after dialysis. In this connection the gel filtration chromatography step can be replaced by ion exchange chromatography on S-Sepharose fast flow. It is also proposed that a dye chromatography on a Blue Trisacryl column be carried out before the ion exchange chromatography.

A process for the purification of recombinant EPO is described by Nobuo, I. et al., J. Biochem. 107 (1990) 352–359. In this process EPO is treated however with a solution of Tween® 20, phenylmethylsulfonyl fluoride, ethylmaleimide, pepstatin A, copper sulfate and oxamic acid prior to the purification steps. Publications, including WO 96/35718, to Burg published 14 Nov. 1996, discloses a process for preparing erythropoietin in a serum free fermentation process (EPOsf).

The specific activity of EPO or EPO conjugates in accordance with this invention can be determined by various assays known in the art. The biological activity of the purified EPO proteins of this invention are such that administration of the EPO protein by injection to human patients results in bone marrow cells increasing production of reticulocytes and red blood cells compared to non-injected or control groups of subjects. The biological activity of the EPO proteins, or fragments thereof, obtained and purified in accordance with this invention can be tested by methods according to Annable, et al., Bull. Wld. Hlth. Org. (1972) 47:

99–112 and Pharm. Europa Spec. Issue Erythropoietin BRP Bio 1997(2). Another biological assay for determining the activity of EPO protein, the normocythaemic mouse assay, is described in Example 6.

The invention will be better understood by reference to the following examples which illustrate but do not limit the invention described herein.

EXAMPLES

Example 1

Fermentation and Purification of Human EPO a) Inoculum Preparation and Fermentation One vial of the Working Cell Bank, originating from an EPO-producing CHO cell line (ATCC CRL8695, disclosed in EP 411 678 (Genetics Institute) can be used) is taken from the gas phase of the liquid nitrogen storage tank. The cells are transferred into glass spinner flasks and cultivated in a hydrogen carbonate-buffered medium in a humidified $CO_2$ incubator. Typical serum free media used for the inoculum preparation and fermentation are disclosed in European Patent Application 513 738, to Koch published 12 Jun. 1992, or WO 96/35718, to Burg published 14 Nov. 1996, for example contain as medium DMEM/F12 (e.g. JRH Biosciences/Hazleton Biologics, Denver, US, order No. 57–736) and additionally sodium hydrogencarbonate, L+glutamine, D+glucose, recombinant insulin, sodium selenite, diaminobutane, hydrocortisone, iron(II) sulfate, asparagine, aspartic acid, serine and a stabilizer for mammalian cells such as e.g. polyvinyl alcohol, methyl cellulose, polydextran, poly(ethylene glycol), Pluronic F68, plasma expander polygelin (HEMACCEL®) or polyvinyl pyrrolidone (WO 96/35718).

The cultures are microscopically checked for the absence of contaminating microorganisms, and the cell densities are determined. These tests are performed at each splitting step.

After the initial growth period, the cell culture is diluted with fresh medium to the starting cell density and undergoes another growth cycle. This procedure is repeated until a culture volume of approximately 2 l per glass spinner flask has been obtained. After approx. 12 doublings 1 to 5 liter of this culture is available which then is used as inoculum for the 10 l inoculum fermenter.

After 3–5 days, the culture in the 10 l fermenter can be used as inoculum for the 100 l inoculum fermenter.

After additional 3–5 days of cultivation, the culture in the 100 l fermenter can be used as inoculum for the 1000 l production fermenter.

b) Harvesting and Cell Separation

A batch refeed process is used, i.e. when the desired cell density is reached, approx. 80% of the culture is harvested. The remaining culture is replenished with fresh culture medium and cultivated until the next harvest. One production run consists of a maximum of 10 subsequent harvests: 9 partial harvests and 1 overall harvest at the end of fermentation. Harvesting takes place every 3–4 days.

The determined harvest volume is transferred into a cooled vessel. The cells are removed by centrifugation or filtration and discarded. The EPO containing supernatant of the centrifugation step is in-line filtered and collected in a second cooled vessel. Each harvest is processed separately during purification.

A typical process for the purification of EPO-protein is disclosed in WO 96/35718, to Burg published Nov. 14, 1996. The purification process is explained in the following.

a) Blue Sepharose Chromatography

Blue Sepharose (Pharmacia) consists of Sepharose beads to the surface of which the Cibacron blue dye is covalently bound. Since EPO binds more strongly to Blue Sepharose than most non-proteinaceous contaminants, some proteinaceous impurities and PVA, EPO can be enriched in this step. The elution of the Blue Sepharose column is performed by increasing the salt concentration as well as the pH.

The column is filled with 80–100 l of Blue Sepharose, regenerated with NaOH and equilibrated with equilibration buffer (sodium/calcium chloride and sodium acetate). The acidified and filtered fermenter supernatant is loaded. After completion of the loading, the column is washed first with a buffer similar to the equilibration buffer containing a higher sodium chloride concentration and consecutively with a Tris-base buffer. The product is eluted with a Tris-base buffer and collected in a single fraction in accordance with the master elution profile.

b) Butyl Toyopearl Chromatography

The Butyl Toyopearl 650 C (Toso Haas) is a polystyrene based matrix to which aliphatic butyl-residues are covalently coupled. Since EPO binds more strongly to this gel than most of the impurities and PVA, it has to be eluted with a buffer containing isopropanol.

The column is packed with 30–40 l of Butyl Toyopearl 650 C, regenerated with NaOH, washed with a Tris-base buffer and equilibrated with a Tris-base buffer containing isopropanol.

The Blue Sepharose eluate is adjusted to the concentration of isopropanol in the column equilibration buffer and loaded onto the column. Then the column is washed with equilibration buffer with increased isopropanol concentration. The product is eluted with elution buffer (Tris-base buffer with high isopropanol content) and collected in a single fraction in accordance with the master elution profile.

c) Hydroxyapatite Ultrogel Chromatography

The Hydroxyapatite Ultrogel (Biosepra) consists of hydroxyapatite which is incorporated in an agarose matrix to improve the mechanical properties. EPO has a low affinity to hydroxyapatite and can therefore be eluted at lower phosphate concentrations than protein impurities.

The column is filled with 30–40 l of Hydroxyapatite Ultrogel and regenerated with a potassium phosphate/calcium chloride buffer and NaOH followed by a Tris-base buffer. Then it is equilibrated with a Tris-base buffer containing a low amount of isopropanol and sodium chloride.

The EPO containing eluate of the Butyl Toyopearl chromatography is loaded onto the column. Subsequently the column is washed with equilibration buffer and a Tris-base buffer without isopropanol and sodium chloride. The product is eluted with a Tris-base buffer containing a low concentration of potassium phosphate and collected in a single fraction in accordance with the master elution profile.

d) Reversed Phase HPLC on Vydac C4

The RP-HPLC material Vydac C4 (Vydac)consists of silica gel particles, the surfaces of which carry C4-alkyl chains. The separation of EPO from the proteinaceous impurities is based on differences in the strength of hydrophobic interactions. Elution is performed with an acetonitrile gradient in diluted trifluoroacetic acid.

Preparative HPLC is performed using a stainless steel column (filled with 2.8 to 3.2 liter of Vydac C4 silicagel).

The Hydroxyapatite Ultrogel eluate is acidified by adding trifluoro-acetic acid and loaded onto the Vydac C4 column. For washing and elution an acetonitrile gradient in diluted trifluoroacetic acid is used. Fractions are collected and immediately neutralized with phosphate buffer. The EPO fractions which are within the IPC limits are pooled.

e) DEAE Sepharose Chromatography

The DEAE Sepharose (Pharmacia) material consists of diethylaminoethyl (DEAE)-groups which are covalently bound to the surface of Sepharose beads. The binding of EPO to the DEAE groups is mediated by ionic interactions. Acetonitrile and trifluoroacetic acid pass through the column without being retained. After these substances have been washed off, trace impurities are removed by washing the column with acetate buffer at a low pH. Then the column is washed with neutral phosphate buffer and EPO is eluted with a buffer with increased ionic strength.

The column is packed with DEAE Sepharose fast flow. The column volume is adjusted to assure an EPO load in the range of 3–10 mg EPO/ml gel. The column is washed with water and equilibration buffer (sodium/potassium phosphate). The pooled fractions of the HPLC eluate are loaded and the column is washed with equilibration buffer. Then the column is washed with washing buffer (sodium acetate buffer) followed by washing with equilibration buffer. Subsequently, EPO is eluted from the column with elution buffer (sodium chloride, sodium/potassium phosphate) and collected in a single fraction in accordance with the master elution profile.

The eluate of the DEAE Sepharose column is adjusted to the specified conductivity. The resulting drug substance is sterile filtered into Teflon bottles and stored at −70° C.

Example 2

Pegylation of EPO with mPEG-SBA

EPO purified in accordance with the serum free procedure of Example 1 (EPOsf) was homogeneous as determined by analytical methods and showed the typical isoform pattern consisting of 8 isoforms. It had a specific biological activity of 190,000 IU/mg as determined by the normocythaemic mouse assay. The pegylation reagent used was a methoxy-PEG-SBA, which is a compound of Formula II in which R is methyl; x is 3; and m is from 650 to 750 (avg. about 680, corresponding to an average molecular weight of about 30 kDa).

Pegylation Reaction

To one hundred milligrams of EPOsf (9.71 ml of a 10.3 mg/ml EPOsf stock, 5.48 µmol) 10 ml of 0.1 M potassium phosphate buffer, pH, 7.5 containing 506 mg of 30 kDa methoxy-PEG-SBA (16.5 µmol) (obtained from Shearwater Polymers, Inc., Huntsville, Ala.) was added and mixed for 2 h at room temperature (20–23° C.). The final protein concentration was 5 mg/ml and the protein:PEG reagent ratio was 1:3. After two hours, the reaction was stopped by adjusting the pH to 4.5 with glacial acetic acid and stored at −20° C., until ready for purification.

Purification

1. Conjugate Mixture: Approximately 28 ml of SP-SEPHAROSE FF (sulfo-propyl cation exchange resin) was packed into an AMICON glass column (2.2×7.5 cm) and equilibrated with 20 mM acetate buffer pH, 4.5 at a flowrate of 150 ml/h. Six milliliters of the reaction mixture containing 30 mg protein was diluted 5-fold with the equilibration buffer and applied onto the column. Unadsorbed materials were washed away with the buffer and the adsorbed PEG conjugate mixture was eluted from the column with 0.175 M NaCl in the equilibration buffer. Unmodified EPOsf still remaining on the column was eluted with 750 mM NaCl. Column was reequilibrated in the starting buffer. Samples were analyzed by SDS-PAGE and their degree of pegylation were determined. It was found that the 0.175 M NaCl eluate contained, mono- as well as di- and trace amounts of the tri-pegylated species, whereas the 750 mM NaCl eluate contained unmodified EPOsf.

2. Di-PEG and Mono-PEG-EPOsf: The purified conjugate mixture eluted from the column in the previous step was diluted 4-fold with the buffer and reapplied onto the column and washed as described. Di-PEG-EPOsf and mono-PEG-EPOsf were separately eluted from the column with 0.1 M NaCl and 0.175 M NaCl, respectively. Elution was also performed with 750 mM NaCl to elute any remaining unmodified EPOsf.

Alternatively, the reaction mixture was diluted 5-fold with the acetate buffer and applied onto the SP-Sepharose column (~0.5 mg protein/ml gel). Column was washed and adsorbed mono-PEG-EPOsf, di-PEG-EPOsf and unmodified EPOsf were eluted as described in the previous section.

Results

PEG-EPOsf was synthesized by chemically conjugating a linear PEG molecule with a number average molecular weight of 30 kDa. PEG-EPOsf was derived from the reaction between the primary amino groups of EPOsf and the succinimidyl ester derivative of a 30 kDa PEG-butyric acid, resulting in an amide bond.

Results are summarized in Table1. Purified conjugate mixture comprised of mono- and di-PEG-EPOsf and was free of unmodified EPOsf as determined by SDS-PAGE analysis. Conjugate mixture accounted for 23.4 mg or 78% of the starting material. Cation exchange chromatographic separation of mono- and di-PEG-EPOsf indicated that mono- to di-PEG ratio in the conjugate mixture was almost 1:1. After completion of the reaction, ratio of the individual components of Mono: Di: Unmodified were 40: 38: 20 (%). Overall yield was almost quantitative.

TABLE 1

Summary of results of EPOsf pegylation

| Sample | Protein (mg) | Yield (%) |
|---|---|---|
| Rxn. Mix. | 30 | 100 |
| Mono- | 12.0 | 40 |
| Di- | 11.4 | 38 |
| Unmod. | 6.0 | 20 |
| Conju. Mix. | 23.4 | 78 |

Example 3

Pegylation of EPO with mPEG-SPA

A different aliquot of the EPOsf used in Example 2 was reacted with 30 kDa methoxy-PEG-SPA (Shearwater Polymers, Inc., Huntsville, Ala.). Reaction was performed at a protein:reagent ratio of 1:2 and purification techniques were in accordance with Example 2. Primarily the mono-pegylated species was produced.

Example 4

Covalent Linking of thiol groups to EPO

This example discloses the determination of reaction conditions for the covalent linking of thiol groups to EPO. To determine the conditions, different amounts of a reagent containing a blocked thiol group, here SATA or SATP (dissolved in DMSO ad 10 mg/ml) were added to the EPO solution, here to 1 ml of 5 mg/ml EPO in 10 mM potassium phosphate, 50 mM NaCl, pH 7.3. The reaction was stirred for about 30 minutes (25° C.) and stopped by addition of 1 M lysine solution at 10 mM. Excess amounts of SATA and SATP were removed by dialysis against 10 mM potassium phosphate, 50 mM NaCl and 2 mM EDTA, pH 6.2. After removal of the protecting acetyl group with hydroxylamine, the number of thiol groups covalently linked to EPO was determined photometrically with dithiodipyridine according to the method described by Grasetti, D. R. and Murray, J. F. in J. Appl. Biochem. Biotechnol. 119, page 41–49 (1967).

The number of thiol groups covalently linked per EPO molecule is shown below.

| Molar ratio EPO:SATA or SATP | Mol thiol groups/mol EPO |
| --- | --- |
| EPO:SATA = 1:3 | 1.5 |
| EPO:SATA = 1:5 | 2.4 |
| EPO:SATA = 1:6 | 3.2 |
| EPO:SATP = 1:3 | 1.3 |
| EPO:SATP = 1:4 | 2.5 |
| EPO:SATP = 1:6 | 3.7 |

Example 5

Modification of Activated EPO with Methoxy-PEG-Maleimide

A) Activation of EPO 100 mg EPO produced according to Example 1 (190,000 IU/ mg as determined by the normocythaemic mouse assay) were activated with SATA (molar ratio: EPO/SATA=1/5) according to Example 2. The resulting EPO ("activated EPO") carrying covalently linked blocked thiol groups was separated from by-products like N-hydroxy-succinimide or non-reacted SATA by dialysis as described in Example 1. A solution of 4.5 mg/ml activated EPO in 10 mM potassium phosphate, 50 mM NaCl, 2 mM EDTA, pH 6.2 was obtained.

B) Pegylation of activated EPO 380 mg methoxy-PEG-maleimide having the "most preferred" structure illustrated above (MW 30.000; Shearwater Polymers, Inc., Huntsville (Ala., USA)) was dissolved in the above solution containing 95 mg activated EPO (4.5 mg/ml in 10 mM potassium phosphate, 50 mM NaCl, 2 mM EDTA, pH 6.2). The resulting molar ratio between activated EPO and methoxy-PEG-maleimide in the solution was 1:4. By addition of 1 M aqueous hydroxylamine solution ad 30 mM, pH 6.2 to the above solution the covalently linked blocked thiol groups of activated EPO were de-blocked. The resulting activated EPO in the reaction mixture of the solution contained free thiol (—SH) groups. De-blocking of the thiol groups was followed immediately by the coupling reaction between the activated EPO now containing free thiol (—SH) groups and methoxy-PEG-maleimide for 90 minutes (stirring, 25° C.). The coupling reaction was stopped by addition of 0.2 M aqueous cysteine solution ad 2 mM to the reaction mixture. After 30 minutes excess free thiol groups of the activated EPO which did not react with methoxy-PEG-maleimide were blocked by addition of a 0.5 M N-methyl-maleimide solution in DMSO to reach a concentration of 5 mM. After 30 minutes the resulting reaction mixture now containing pegylated EPO species was dialyzed against 10 mM potassium phosphate, pH 7.5 for ≦15 hours.

C) Purification of Pegylated EPO Species

For separation of the pegylated EPO species from the reaction mixture, the following purification process was performed: A 50 ml Q-Sepharose ff column was equilibrated with 10 mM potassium phosphate, pH 7.5. The reaction mixture obtained in step B) was loaded onto the column (flow rate: 3 column volumes (CV) per hour). In order to separate non-reacted methoxy-PEG-maleimide reagent, the column was washed with 5 CV's of 10 mM potassium phosphate, pH 7.5. Pegylated EPO species were separated by elution with an increasing salt gradient consisting of 5 CV's buffer A (10 mM potassium phosphate, pH 7.5) and 5 CV's buffer B (10 mM potassium phosphate, 500 mM NaCl, pH 7.5) with a flow rate of 3 CV per hour. Based on the NaCl gradient, the pegylated EPO species (tri-, bi- and mono-pegylated EPO species) were eluted first, followed by the non-pegylated EPO species. The fraction of the eluate containing the pegylated EPO species (tri-, di- and mono-pegylated EPO species) was pooled and filtered (sterile filtration with a 0.2 µm filter).

Content and purity of tri-, di- and mono-pegylated EPO species were evaluated on Coomassie-stained SDS-PAA gels (Laemmli, Nature 227, 680–685 (1970)) while protein concentrations were measured at 280 nm according the Beer-Lambert law. The apparent molecular weights of the EPO species determined by SDS-PAA electrophoresis were about 68 kDa (mono-pegylated EPO species), about 98 kDa (di-pegylated EPO species), and about 128 kDa (tri-pegylated EPO species).

Further separation of the tri-, di and mono-pegylated EPO species can be achieved by chromatography, e.g. by size exclusion chromatography (Superdex, pg 200; Pharmacia). The determination of in-vivo biological activity of the eluate containing tri- di- and mono-pegylated species was performed by the method described below.

Example 6

In-Vivo Activity of Pegylated EPO Determined by the Normocythaemic Mouse Assay The normocythaemic mouse bioassay is known in the art (Pharm. Europa Spec. Issue Erythropoietin BRP Bio 1997 (2)) and a method in the monography of erythropoietin of Ph. Eur. BRP. The samples were diluted with BSA-PBS. Normal healthy mice, 7–15 weeks old, were administered s.c. 0.2 ml of the EPO-fraction containing non-pegylated EPO or tri-, di- or mono-pegylated EPO from Example 2 or 3. Over a period of 6 days, blood was drawn by puncture of the tail vein and diluted such that 1 µl of blood was present in 1 ml of an 0.15 µmol acridine orange staining solution. The staining time was 3 to 10 minutes. The reticulocyte counts were carried out microfluorometrically in a flow cytometer by analysis of the red fluorescence histogram. The reticulocyte counts were given in terms of absolute figures (per 30,000 blood cells analyzed). For the data presented, each group consisted of 5 mice per day, and the mice were bled only once.

In separate experiments, a single dose of unmodified EPO (25 ng of EPO), the PEG(SBA)-EPO mixture from Example 2 (10 ng of conjugate), mono- and di-pegylated EPOs from Example 2 (10 ng of conjugate), the PEG(SPA)-EPO from Example 3 (10 ng of conjugate), and buffer solution were administered to mice. The results are shown in Table 2. The results show the superior activity and the prolonged half life of the pegylated EPO species indicated by the significantly increased amounts of reticulocytes and the shift of the reticulocytes count maximum using the same dose per mouse (10 ng), compared to a dose of 25 ng for unmodified EPO.

TABLE 2

|  | EPO (Not modified) | 30 kDa SPA PEG | Mono 30K SBA | Di 30K SBA | PEG-EPO SBA Conjugate Mixture | Control Buffer |
| --- | --- | --- | --- | --- | --- | --- |
| 72 h | 1000 | 1393 | 1411 | 994 | 1328 | 857 |
| 96 h | 500 | 1406 | 1501 | 926 | 1338 | 697 |
| 120 h | ~200 | 1100 | 1182 | 791 | 944 | 701 |
| 144 h | ~0 | 535 | 607 | 665 | 660 | 708 |

Example 7

Preparation of Predominantly Mono-PEG-EPO

Pegylation Reaction

Starting with 100 mg (5.48 µmol) of EPOsf in 100 mM potassium phosphate buffer pH 7.5 prepared in accordance with Example 1, there was added 329 mg (10.96 µmol) of 30 kDa PEG-SBA reagent dissolved in 3 ml 1 mM HCL. Enough 100 mM potassium phosphate buffer pH 7.5 was added to make the reaction mixture volume to 20 ml. The final protein concentration was 5 mg/ml and the protein: PEG reagent ratio was 1:2. The reaction mixture was mixed for 2 h at ambient temperature (20–22° C.). After 2 h, the reaction was stopped by adjusting the pH to 4.5 with glacial acetic acid and stored frozen at −20° C. until ready for purification.

Purification

The reaction mixture from the previous step was diluted 1:5 with 10 mM sodium acetate, pH 4.5 and applied to 300 ml SP-Sepharose FF (sulfopropyl cation exchange resin) packed into a 4.2×19 cm column. The column was previously equilibrated with the same buffer. Column effluents were monitored at 280 nm with a Gilson UV monitor and recorded with a Kipp and Zonen recorder. The column was washed with 300 ml or 1 bed volume of equilibration buffer to remove excess reagents, reaction byproducts and oligomeric PEG-EPO. It was followed by washing with 2 bed volumes of 100 mM NaCl to remove di-PEG-EPO. Mono-PEG-EPO was then eluted with 200 mM NaCl. During elution of the mono-PEG-EPO, the first 50 ml of the protein peak was discarded and the mono-PEG-EPO was collected as a 150 ml fraction. Unmodified EPOsf remaining on the column was eluted with 750 mM NaCl. All elution buffers were made in the equilibration buffer. All eluted samples were analyzed by SDS-PAGE and by high performance Size Exclusion Chromatography (SEC). The mono-PEG-EPO pool obtained from the 150 ml fraction, which had no detectable unmodified EPOsf, was then concentrated to ~4.5–7.5 mg/ml and diafiltered into the storage buffer, 10 mM potassium phosphate, 100 mM NaCl, pH 7.5. Concentration/Diafiltration was performed with Millipore Labscale TFF System fitted with 50 kDa cut off Millipore Pellicon XL Biomax 50 membrane at ambient temperature. Concentrated mono-PEG-EPO was sterile filtered and stored frozen at −20° C.

Approximately 75% of EPOsf was pegylated. After purification, total yield was ~30% mono-PEG-EPO with no detectable unmodified EPOsf and around 25% di-PEG-EPO. Oligomers, and unpegylated EPOsf accounted for the remaining protein. The mono-PEG-EPO pool obtained from the 150 ml fraction contained approximately 90% mono-PEG-EPO and approximately 10% di-PEG-EPO.

Example 8

Thermostability of EPO and Pegylated EPO in Various Formulations: Analysis by DSC (Differential Scanning Calorimetry)

It is generally accepted that the transition temperature of thermal denaturation measured by differential scanning calorimetry is a valid indicator for the thermostability of proteins. Erythropoietin or pegylated erythropoietin solutions with concentrations between 0.6 and 1.2 mg/ml were analyzed in various buffers with or without stabilizers by means of a Nano-DSC (Calorimetric Sciences Corporation, Utah, USA) at a heating rate of 2 K/min. An increase in transition temperature indicates an increase in thermal stability of the protein. The measured temperature values should not be understood as absolute values but rather represent differences in the stability of the individual formulations relative to one another.

In order to define the optimal pH of the formulation, the pH-dependence of the thermal denaturation of pegylated erythropoietin in the range between 4 and 9 was studied. The protein samples were analyzed in 30 mM $Na_2HPO_4$, 30 mM sodium citrate, 30 mM borate. FIG. 1 shows a plateau of maximal transition temperature between about pH 6 to about pH 9 and a sharp decrease below pH 5.5. This indicates that the optimal pH for maximal thermal stability lies above pH 5.5. (FIG. 3).

Figure 4:
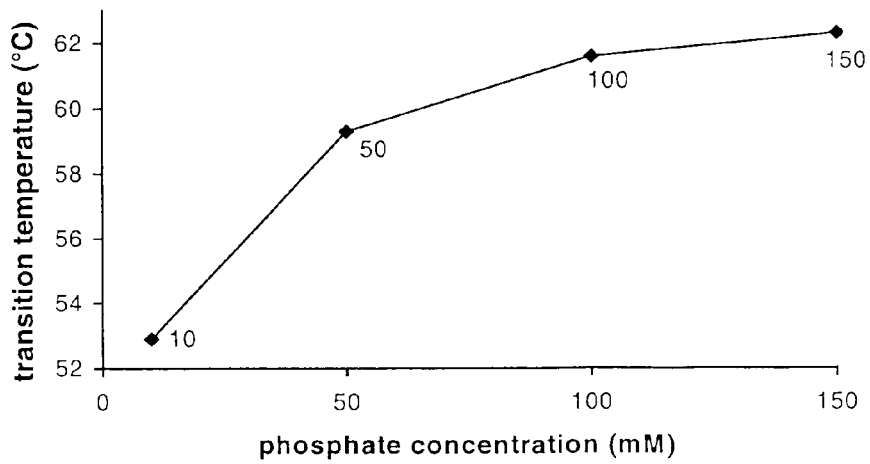
FIG. 4: Influence of ionic strength on thermal stability. The transition temperature is plotted against the phosphate concentration.

In order to investigate the effect of ionic strength, the phosphate concentration dependence of thermal denaturation was determined. FIG. 4 shows that the thermal stability increases with an increase in ionic strength of the formulation.

The influence of the buffer substance was also investigated by DSC. From FIG. 5 one can see that the most suitable buffers or additives for a high thermal stability are sulfate, citrate or phosphate. Glycine, which is used as a buffer in currently available formulations (see above) is not very suitable.

Figure 6:
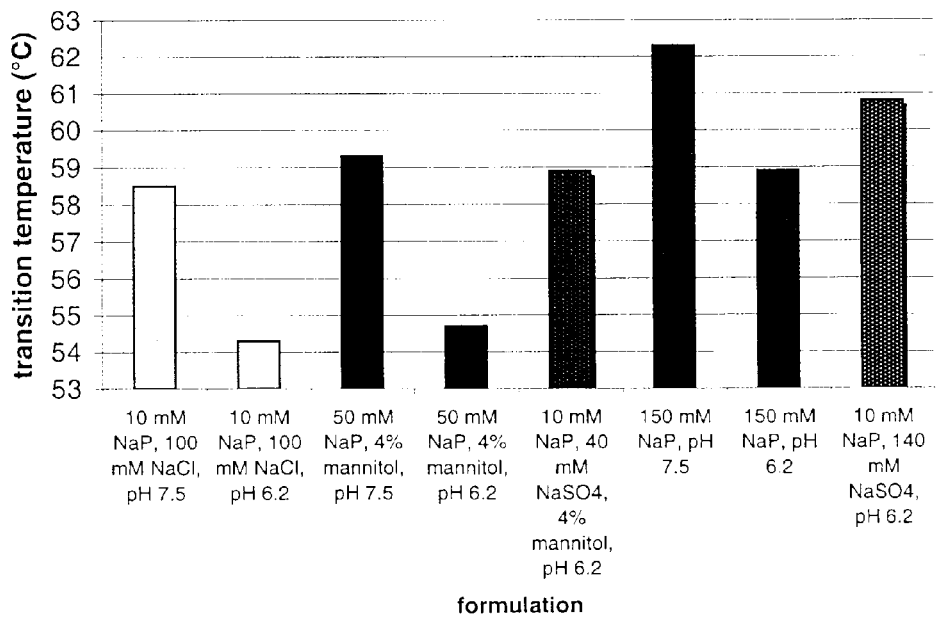
FIG. 6: shows that sulfate is also a suitable buffer/additive at low pH (e.g. pH 6.2), whereas phosphate is less suitable at pH 6.2 compared to pH 7.5. This shows that sulfate keeps the thermal stability high, even at low pH.

FIG. 6 shows that sulfate is also a suitable buffer/additive at low pH (e.g. pH 6.2), whereas phosphate is less suitable at pH 6.2 compared to pH 7.5. This shows that sulfate keeps the thermal stability high, even at low pH. This finding allows a formulation at a pH between 6.0 and 6.5, without severe losses in thermal stability of erythropoietin.

Example 9

Aggregation of EPO and Peg-EPO under Thermal Stress: Analysis by SDS-PAGE (Sodium Dodecyl Sulphate Polyacrylamide Gel Electrophoresis)

Figure 5:
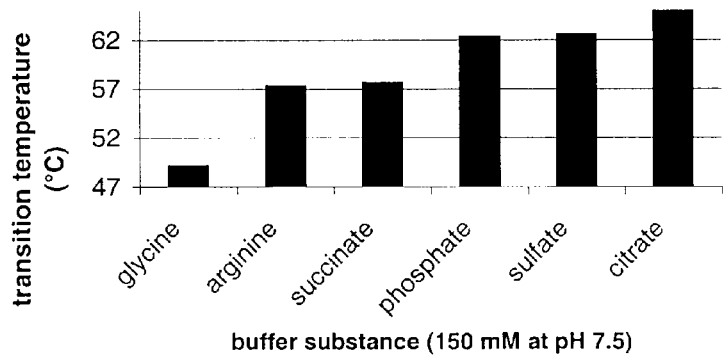
FIG. 5: Dependence of thermal stability on buffer substance.

In order to investigate the effect of heat stress on the erythropoietin protein, samples in different formulations were exposed to heat stress (20 min 80° C.) and analyzed by sodium dodecyl sulphate polyacrylamide gel electrophoresis (SDS-PAGE) under reducing (with DTT in sample buffer) and non-reducing (w/o DTT in sample buffer) conditions. This method allows the detection of covalent aggregate formation. As outlined above, aggregate formation is one of the major degradation pathways of proteins and therefore should be prevented in pharmaceutical formulations of proteins. Aggregates that are detectable in the absence of reducing agent (e.g. DTT) and not detectable in the presence of reducing agent are highly likely to be formed by incorrect disulfide bridging, an oxidation reaction, under heat stress. FIG. 5 shows the pH dependency of aggregation under heat stress. This experiment clearly shows that the formation of aggregates is suppressed at a pH below 6.5. The higher the pH, the higher the amount of aggregation. Most of the aggregates that are formed can be reduced by treatment of the samples with a reducing agent during SDS-PAGE, suggesting that a great portion of the aggregates that are formed under heat stress are disulfide-bridged dimers, oligomers and higher order aggregates. Taken together, his indicates that the formation of aggregates can be prevented to a great extent by keeping the pH of the formulation at or below pH 6.5.

Figure 7:
FIG. 7: Dependency of peg-EPO aggregation on pH. Peg-EPO samples after heat stress (as described above) were analyzed by SDS-PAGE. Proteins were stained with silver. Lane 1: molecular weight standard. Lane 2: pH 5. Lane 3: pH 5, reduced. Lane 4: pH 6. Lane 5: pH 6, reduced. Lane 6: pH 6.5. Lane 7: pH 6.5, reduced. Lane 8: pH 7. Lane 9: pH 7, reduced. Lane 10: peg-EPO, unstressed.

FIG. 7: Dependency of peg-EPO aggregation on pH. Peg-EPO samples after heat stress (as described above) were analyzed by SDS-PAGE. Proteins were stained with silver. Lane 1: molecular weight standard. Lane 2: pH 5. Lane 3: pH 5, reduced. Lane 4: pH 6. Lane 5: pH 6, reduced. Lane 6: pH 6.5. Lane 7: pH 6.5, reduced. Lane 8: pH 7. Lane 9: pH 7, reduced. Lane 10: peg-EPO, unstressed.

Figure 8:
FIG. 8 shows that the use of 1 mg/ml acetylcysteine as an antioxidant prevents the formation of aggregates under heat stress. Aggregation of pegEPO under heat stress (20 min 80° C.): Lane 1: pegEPO at pH 7.5, un-stressed; Lane 2: pegEPO at pH 7.5, stressed: Lane 3: pegEPO at pH 6.2, stressed; Lane 4: pegEPO at pH 6.2, stressed, reduced; Lane 5: pegEPO at pH 7.5, +1 mg/ml N-Acetyl-cysteine, stressed; Lane 6: pegEPO at pH 7.5, +1 mg/ml N-Acetyl-cysteine, stressed, reduced

The formation of aggregates can also be prevented by the use of antioxidants. FIG. 8 shows that the use of 1 mg/ml acetylcysteine as an antioxidant prevents the formation of aggregates under heat stress. Therefore, it is useful to use an antioxidant, like e.g. acetylcysteine at a low pH, e.g. pH 6.2, to prevent aggregate formation under heat stress.

FIG. 6: Peg-EPO aggregation can be prevented by pH 6.2 and/or acetylcysteine. Peg-EPO samples after heat stress (as described above) were analyzed by SDS-PAGE. Proteins were stained with silver. Lane 1: peg-EPO, unstressed. Lane 2: pH 7.5, stressed. Lane 3: pH 6.2, stressed. Lane 4: pH 6.2, stressed, reduced. Lane 5: pH 7.5, 1 mg/ml acetylcysteine, stressed. Lane 6: pH 7.5, 1 mg/ml acetylcysteine, stressed, reduced.

Example 10

Stability of Peg-EPO in Various Formulations at 4, 25, 30 and 40° C.

Pegylated EPO in various formulations is incubated at several temperatures. At indicated time points, samples are taken and the stability is assessed by reversed phase high performance chromatography (rpHPLC), high performance size exclusion chromatography (SEC) and sodium dodecyl sulphate polyacrylamide gel electrophoresis (SDS-PAGE). Table 3 compares the stability of peg-EPO in various formulations at several temperatures. These data clearly show the superiority of the herein enclosed formulations regarding protein recovery and aggregation.

TABLE 3

Stability of peg-EPO in various formulations at several temperatures:

| Formulation | pegEPO | % recovery after six months at | | | | Aggregation at 30° C. detectable |
|---|---|---|---|---|---|---|
| * | (µg/ml) | 4° C. | 25° C. | 30° C. | 40° C. | (+/−) |
| A | 10 | 92 | 91 | n.d. | 39 | n.d. |
| B | 50 | 97 | 98 | 97 | 78 | − |
| C | 50 | 95 | 79 | 79 | 52 | + |
| E | 50 | 103 | 102 | 100 | 87 | − |
| A | 100 | 96 | 97 | n.d. | 50 | n.d. |
| B | 400 | 101 | 101 | 101 | 77 | − |
| C | 400 | 100 | 94 | 90 | 56 | + |

TABLE 3-continued

Stability of peg-EPO in various formulations at several temperatures:

| Formulation | pegEPO | % recovery after six months at | | | | Aggregation at 30° C. detectable |
|---|---|---|---|---|---|---|
| * | (µg/ml) | 4° C. | 25° C. | 30° C. | 40° C. | (+/−) |
| D | 400 | 98 | 96 | 93 | 73 | − |
| E | 400 | 99 | 98 | 100 | 66 | − |

* the formulations are:
formulation A: 10 mM sodium phosphate, 100 mM sodium chloride, pH 7.5.
formulation B: 10 mM sodium phosphate, 40 mM sodium sulfate, 3% (w/v) mannitol, pH 6.2.
formulation C: 10 mM sodium phosphate, 100 mM NaCl, pH 7.0.
formulation D: 10 mM sodium phosphate, 120 mM sodium sulfate, pH 6.2
formulation E: 40 mM arginine, 30 mM sodium sulfate, 3% mannitol, 1 mM $CaCl_2$, pH 6.2.

Example 11

Optimized Formulations Suppress Oxidation of Methionine54 in EPO Protein, Methionine as an Anti-Oxidant Pegylated EPO in various formulations is incubated at several temperatures. After 6 months, samples are taken and the degree of methionine54 oxidation is determined, as follows. Briefly, EPO samples are treated with the endoproteinase LysC. Resulting peptides are separated by reversed phase chromatography. The ratio of peptide T8oxidized (containing the oxidized methionine54) to peptide T8 (containing non-oxidized methionine54) is calculated. The data are summarized in table 4.

TABLE 4

Degree of methionine54 oxidation of EPO protein in various formulations after six months at indicated temperatures

| Formulation | pegEPO | % oxidized methionine54 | | | |
|---|---|---|---|---|---|
| * | (µg/ml) | 4° C. | 25° C. | 30° C. | 40° C. |
| A | 400 | 2.00 | 15.89 | 24.89 | 37.89 |
| B | 400 | 2.33 | 6.55 | 12.88 | 30.24 |
| C | 400 | 2.51 | 2.95 | 5.99 | 14.4 |
| A | 50 | 5.37 | 21.36 | 30.62 | 48.05 |
| B | 50 | 3.44 | 13.38 | 16.59 | 30.83 |
| C | 50 | 4.41 | 5.52 | 10.01 | 15.62 |

* the formulations are listed below
formulation A: 10 mM sodium phosphate, 100 mM sodium chloride, pH 7.0
formulation B: 10 mM sodium phosphate, 40 mM sodium sulfate, 3% (w/v) mannitol, pH 6.2.
formulation C: 10 mM sodium phosphate, 40 mM sodium sulfate, 3% (w/v) mannitol, 1 mM methionine, pH 6.2.

These data clearly show that the preferred formulation of the present invention (10 mM sodium phosphate, 40 mM sodium sulfate, 3% (w/v) mannitol, pH 6.2) is superior to other formulations like 10 mM sodium phosphate, 100 mM NaCl, pH 7.0, regarding the degree of methionine54 oxidation. The addition of 1 or 10 mM methionine into the formulation clearly suppresses the oxidation of methionine54. Therefore, methionine acts as an anti-oxidant and stabilizes EPO.

Example 12

Sialic Acid Content of Peg-EPO Samples in Various Formulations

Figure 9:
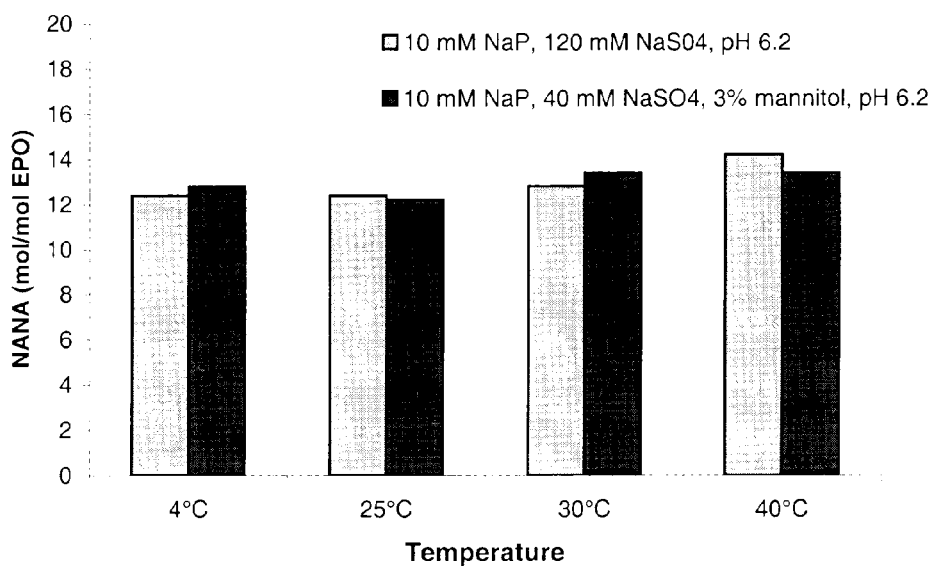
FIG. 9: Sialic acid (NANA) content of peg-EPO samples in new formulations, stored for six months at various temperatures.

In order to analyze the integrity of the carbohydrate structure of the peg-EPO glycoprotein, the sialic acid content of peg-EPO samples in optimized formulations after storage for 6 months at various temperatures was analyzed by standard techniques. These data show that the integrity of the carbohydrate structure is not negatively influenced by storage of the protein in the new formulations described herein (FIG. 9).

Example 13

Figure 10:
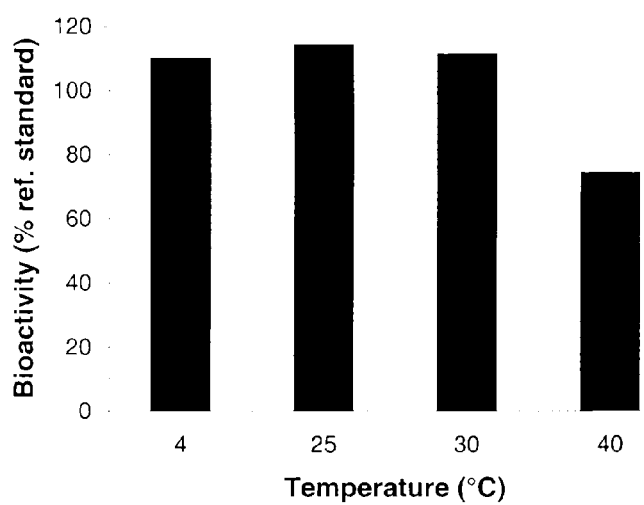
FIG. 10: Mouse bioactivity assay of peg-EPO samples after storage in 10 mM sodium phosphate, 40 mM sodium sulfate, 3% (w/v) mannitol, pH 6.2 for 6 months at several temperatures.

Bioactivity of Pegylated EPO after Storage at Elevated Temperature for Prolonged Time Periods In order to proof that storage of peg-EPO in 10 mM sodium phosphate, 40 mM sodium sulfate, 3% (w/v) mannitol, pH 6.2, does not negatively influence bioactivity in vivo, a standard mouse EPO assay was carried out (see Example 6). Peg-EPO samples stored for 6 months in 10 mM sodium phosphate, 40 mM sodium sulfate, 3% (w/v) mannitol, pH 6.2, at the indicated temperatures, showed no loss of in vivo activity after storage at 4, 25 and 30° C. compared to fresh reference standard (FIG. 10).

Example 14

Aggregate Content of Peg-EPO after Storage at Elevated Temperature for 6 Months In order to analyze the aggregate content in peg-EPO samples after storage at elevated temperature in 10 mM sodium phosphate, 40 mM sodium sulfate, 3% (w/v) mannitol, pH 6.2, after 6 months samples where taken and analyzed by size exclusion chromatography.

Figure 11:
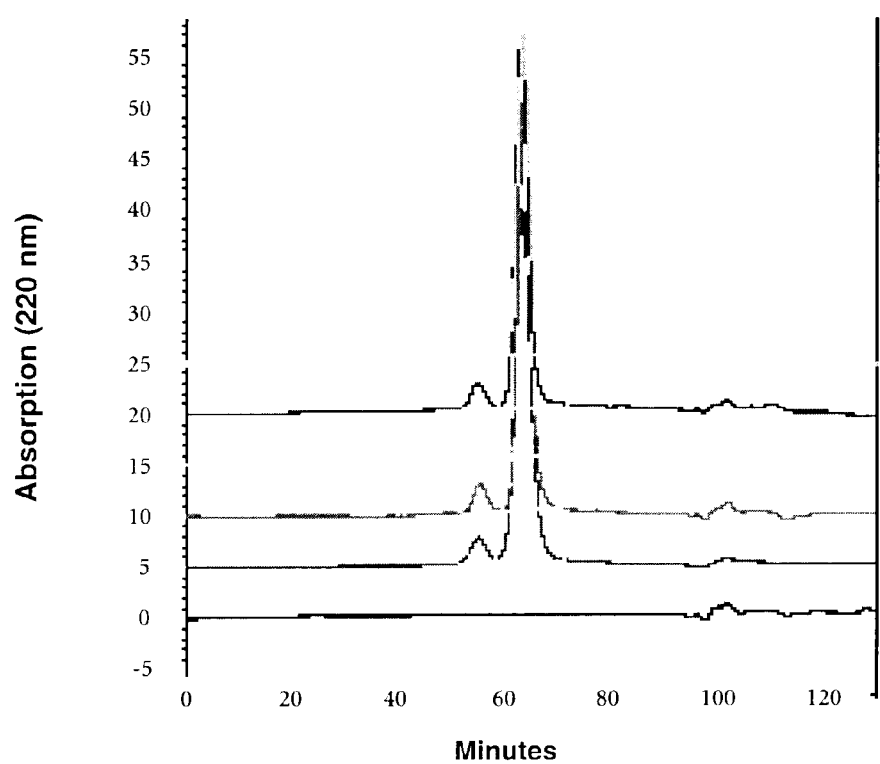
FIG. 11: Size exclusion chromatogram overlay of peg-EPO samples stored for 6 months in 10 mM sodium phosphate, 40 mM sodium sulfate, 3% (w/v) mannitol, pH 6.2 (bottom to top: buffer, starting material, 4° C., 25° C., 30° C. and 40° C.).

No aggregates were detectable at 4, 25 and 30° C., proving the stability of pegylated EPO in the above-mentioned formulations. FIG. 11 shows an overlay of the size exclusion chromatogramms.

---

The invention claimed is:

1. A liquid pharmaceutical composition in the form of an aqueous solution comprising:

(a) an erythropoietin glycoprotein conjugate comprising an erythropoietin protein having at least one free amino group and having the sequence SEQ ID NO: 1 or SEQ ID NO: 2, or having either of said sequences modified by the addition of from 1 to 6 glycosylation sites or by rearrangement of at least one glycosylation site; said erythropoietin protein being covalently linked to from one to three lower-alkoxy poly(ethylene glycol) groups with each poly(ethylene glycol) group being covalently linked to the erythropoietin via a linker of the formula —C(O)—X—S—Y— with the C(O) of the linker forming an amide bond with one of said amino groups; X is —(CH$_2$)$_k$— or —CH$_2$(O—CH$_2$—CH$_2$)$_k$—; k is from 1 to 10; Y is selected from

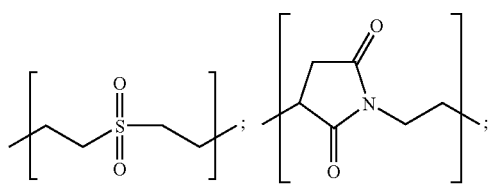

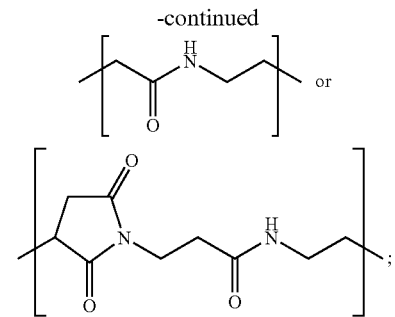

the average molecular weight of each poly(ethylene glycol) moiety being from about 20 kilodaltons to about 40 kilodaltons; and wherein the molecular weight of the erythropoietin conjugate is from about 51 kilodaltons to about 175 kilodaltons, and wherein the amount of erythropoietin protein is from 10 μg per ml to about 10,000 μg per ml of solution;

(b) from 10 to 200 mmol per liter of solution of a multiple charged inorganic anion; and (c) a pharmaceutically acceptable buffer; said anion and said buffer being present in said solution in an amount to provide the solution with a pH of from 5.5 to about 7.0, said liquid composition being stable at room temperature.

2. The composition of claim 1 wherein said conjugate has the formula:

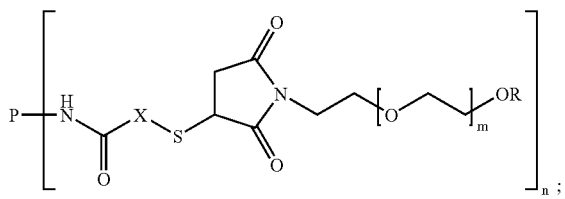

wherein n is an integer from 1 to 3; m is an integer from 450 to 900; R is lower alkyl; X is —(CH$_2$)$_k$— or —CH$_2$(O—CH$_2$—CH$_2$)$_k$—; and P is the erythropoietin glycoprotein without the amino group or groups which form an amide linkage; and k is from 1–10.

3. The composition of claim 1 wherein the conjugate has the formula:

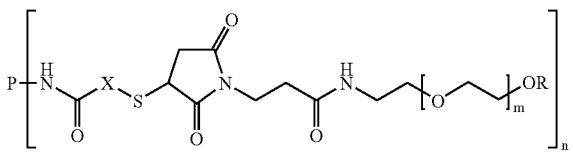

wherein n is an integer from 1 to 3; m is an integer from 450 to 900; R is lower alkyl; X is —(CH$_2$)$_k$— or —CH$_2$(O—CH$_2$—CH$_2$)$_k$—; and P is the erythropoietin glycoprotein without the amino group or groups which form an amide linkage; and k is from 1–10.

4. The composition of claim 1 wherein said solution is an isotonic solution.

5. The composition of claim 1 wherein the anion is an anion of a multiple charged strong inorganic acid.

6. The composition of claim 5 wherein the anion is selected from the group consisting of sulfate or phosphate.

7. The composition of claim 6 wherein the anion is a sulfate anion.

8. The composition of claim 7 wherein the pH is 5.8 to 6.7.

9. The composition of claim 8 wherein the pH is about 6.2.

10. The composition of claim 7 wherein the pH is 6.0 to 6.5.

11. The composition of claim 1 wherein the buffer is a phosphate buffer.

12. The composition of claim 1 wherein the erythropoietin has the amino acid sequence SEQ ID NO:1 or SEQ ID NO:2.

13. The composition of claim 1 wherein the erythropoietin glycoprotein has the sequence SEQ ID NO: 1 or SEQ ID NO: 2 that is modified by the addition of from 1 to 6 glycosylation sites.

14. The composition of claim 13 wherein the sequence of modification is
Asn$^{30}$Thr$^{32}$Val$^{87}$Asn$^{88}$Thr$^{90}$.

15. The composition of claim 1 wherein said erythropoietin glycoprotein has the sequence SEQ ID NO: 1 or SEQ ID NO: 2 that is modified by a rearrangement of at least one glycosylation site.

16. The composition of claim 15, wherein the rearrangement comprises deletion of any of the N-linked glycosylation sites in human erythropoietin with the addition of an N-linked glycosylation site at position 88 of the sequence of human erythropoietin.

17. The composition of claim 1 wherein said solution contains 10 μg to 10,000 μg erythropoietin protein per ml of solution, from 10 to 200 mmol/liter of solution of a sulfate as the multiple charged inorganic anion, and 10 to 50 mmol/liter of solution of a phosphate as the pharmaceutically acceptable buffer, said solution having a pH of from about 6.0 to about 6.5.

18. The composition of claim 17 further comprising up to 20 mM of methionine, and 1–5% of a polyol (w/v).

19. The composition of claim 18 comprising 10 μg to 10,000 μg erythropoietin protein per ml of solution, 40 mmol/liter of solution of the sulfate, 10 mmol/liter of said solution of the phosphate, 10 mM methionine, said composition having a pH of about 6.2, and wherein the polyol is mannitol which is present in the solution at 3% (w/v).

20. The composition of claim 1 wherein said solution contains 10 μg to 10,000 μg erythropoietin protein per ml of solution, the buffer is phosphate which is present at 10 to 50 mmol/liter of solution, said solution further comprising NaCl which is present at 10 to 100 mmol/liter of solution and having a pH of from about 6.0 to about 7.0.

21. The composition of claim 20 wherein the NaCl is present at 100 mmol/liter of solution, the phosphate is present at 10 mmol/l, said solution further comprising 10 mM methionine and having a pH of about 7.0.

22. The composition of claim 1 wherein the amount of erythropoietin protein is 50, 100, 400, 800 or 2,500 μg/ml of solution.

23. The composition of claim 22 comprising 10 mM sodium phosphate and 40 mM sodium sulfate and further comprising 3% mannitol, 10 mM methionine and 0.01% poloxamer 188, and having a pH of about 6.2.

24. The composition of claim 22 comprising 30 mM sodium sulfate and further comprising 3% mannitol, 40 mM arginine, 10 mM methionine, 0.01% poloxamer 188, and a pH of about 6.2.

25. A liquid pharmaceutical composition in the form of an aqueous solution comprising a pegylated erythropoietin glycoprotein conjugate of formula P—[NHCO—(CH$_2$)$_x$—(OCH$_2$CH$_2$)$_m$—OR]$_n$     (I)

wherein
P is an erythropoietin glycoprotein having the sequence SEQ ID NO: 1, SEQ ID NO: 2, or either of these sequences modified by the addition of from 1 to 6 glycosylation sites or by rearrangement of at least one glycosylation site, minus the n amino group of said glycoprotein,
R is lower alkyl,
x is 2 or 3,
m is from about 450 to about 900;
n is from 1 to 3; and
wherein the values of n and m are such that the molecular weight of the conjugate minus the erythropoietin glycoprotein is from 20 kilodaltons to 100 kilodaltons, and wherein the amount of the erythropoietin glycoprotein is from about 10 μg per ml to about 10,000 μg per ml of solution; and
from about 10 to about 200 mmol per liter of solution of a multiple charged inorganic anion and from about 10 to about 50 mmol per liter of solution of a pharmaceutically acceptable buffer, said anion and said buffer being present in said solution in an amount such that the pH of the solution is from about 5.5 to about 7.0.

26. The composition of claim 25 wherein x is 2, m is 650 to 750, n is 1, and R is methyl.

27. The liquid pharmaceutical composition of claim 26 wherein the pegylated erythropoietin conjugate is present in an amount such as to provide about 100.0 μg of erythropoietin protein per mL of solution, the multiple charged inorganic anion is sodium sulfate which is present in an amount of about 5.68 mg/mL, the pharmaceutically acceptable buffer is sodium phosphate which is present in an amount of about 1.38 mg/mL, and wherein the pH of the solution is 6.2±0.2.

28. The liquid pharmaceutical composition of claim 27 further comprising methionine in an amount of about 1.49 mg/mL, mannitol in an amount of about 30.0 mg/mL and poloxamers type 188 in an amount of 0.1 mg/mL.

29. The liquid pharmaceutical composition of claim 26 wherein the pegylated erythropoietin conjugate is present in an amount such as to provide about 400 μg of erythropoietin protein per mL of solution, the multiple charged inorganic anion is sodium sulfate which is present in an amount of about 5.68 mg/mL, the pharmaceutically acceptable buffer is sodium phosphate which is present in an amount of about 1.38 mg/mL, and wherein the pH of the solution is 6.2±0.2.

30. The liquid pharmaceutical composition of claim 29 further comprising methionine in an amount of about 1.49 mg/mL, mannitol in an amount of about 30.0 mg/mL and poloxamers type 188 in an amount of 0.1 mg/mL.

31. The liquid pharmaceutical composition of claim 26 wherein the pegylated erythropoietin conjugate is present in an amount such as to provide about 800.0 μg of erythropoietin protein per mL of solution, the multiple charged inorganic anion is sodium sulphate which is present in an amount of about 5.68 mg/mL, the pharmaceutically acceptable buffer is sodium phosphate which is present in an amount of about 1.38 mg/mL, and wherein the pH of the solution is 6.2±0.2.

32. The liquid pharmaceutical composition of claim 31 further comprising methionine in an amount of about 1.49 mg/mL, mannitol in an amount of about 30.0 mg/mL and poloxamers type 188 in an amount of 0.1 mg/mL.

33. The composition of claim 25 wherein the erythropoietin protein is present at about 25 to about 2,500 μg/ml, the buffer is sodium or potassium phosphate which is present in an amount of about 10 mM, said composition further comprising NaCl which is present in an amount of about 100 mM and having a pH of about 7.0.

34. The composition of claim 25 wherein the solution is an isotonic solution.

35. The composition of claim 25 wherein the anion is an anion of a multiple charged strong inorganic acid.

36. The composition of claim 25 wherein the anion is selected from the group consisting of sulfate or phosphate.

37. The composition of claim 25 wherein the anion is a sulfate anion.

38. The composition of claim 25 wherein the pH is from 5.8 to 6.7.

39. The composition of claim 38 wherein the pH is from 6.0 to 6.5.

40. The composition of claim 39 wherein the pH is about 6.2.

41. The composition of claim 25 wherein the buffer is a phosphate buffer.

42. The composition of claim 25 wherein the erythropoietin glycoprotein has the amino acid sequence SEQ ID NO:1 or SEQ ID NO:2.

43. The composition of claim 42 wherein the erythropoietin glycoprotein has the amino acid sequence SEQ ID NO:1.

44. The composition of claim 25 wherein said solution contains from 10 μg to 10,000 μg erythropoietin protein per ml of solution, from 10 to 200 mmol/liter of solution of a sulfate as the multiple charged inorganic anion, and 10 to 50 mmol/liter of solution of a phosphate as the pharmaceutically acceptable buffer, said solution having a pH of from about 6.0 to about 6.5.

45. The composition of claim 44 further comprising up to 20 mM of methionine, and 1–5% of a polyol (w/v).

46. The composition of claim 45 comprising from 10 μg to 10,000 μg erythropoietin protein per ml of solution, 40 mmol/liter of solution of the sulfate, 10 mmol/liter of said solution of the phosphate, 10 mM methionine, said composition having a pH of about 6.2, and wherein the polyol is mannitol which is present in the solution at 3% (w/v).

47. The composition of claim 25 wherein the solution contains from 10 μg to 10,000 μg erythropoietin protein per ml of solution, the buffer is phosphate which is present at 10 to 50 mmol/liter of solution, said solution further comprising NaCl which is present at 10 to 100 mmol/liter of solution and having a pH of from about 6.0 to about 7.0.

48. The composition of claim 47 wherein the NaCl is present at 100 mmol/liter of solution, the phosphate is present at 10 mmol/l, said solution further comprising 10 mM methionine and having a pH of about 7.0.

49. The composition of claim 25 wherein the amount of erythropoietin protein is 50, 100, 400, 800 or 2,500 μg/ml of solution.

50. The composition of claim 49 comprising 10 mM sodium phosphate and 40 mM sodium sulfate and further comprising 3% mannitol, 10 mM methionine and 0.01% poloxamer 188, and having a pH of about 6.2.

51. The composition of claim 49 comprising 30 mM sodium sulfate and further comprising 3% mannitol, 40 mM arginine, 10 mM methionine, 0.01% poloxamer 188, and a pH of about 6.2.

52. A liquid pharmaceutical composition in the form of an aqueous solution comprising from 10 μg to 10,000 μg per ml of said solution of an erythropoietin glycoprotein product having the in vivo biological activity of causing bone marrow cells to increase production of reticulocytes and red blood cells, from 10 to 100 mmol/liter of solution of sodium sulfate, a buffer, and from 10 to 50 mmol/liter of said solution of arginine, said solution having a pH of from about 6 to about 6.5 and being stable at room temperature.

53. The composition of claim 52 wherein said solution comprises 40 mmol/liter of solution of arginine, 30 mmol/liter of solution of sodium sulfate, said solution further comprising 3% mannitol, 10 mM methionine, and 0.01% poloxamer 188, and having a pH of about 6.2.

54. A liquid pharmaceutical composition in the form of an aqueous solution comprising from about 25 μg to about 2,500 μg per ml of said solution of an erythropoietin glycoprotein product having the in vivo biological activity of causing bone marrow cells to increase production of reticulocytes and red blood cells, about 120 mM of sodium sulfate, and about 10 mM of sodium phosphate, said solution having a pH of about 6.2 and being stable at room temperature.

55. A liquid pharmaceutical composition in the form of an aqueous solution comprising from about 25 μg to about 2,500 μg per ml of said solution of an erythropoietin glycoprotein product having the in vivo biological activity of causing bone marrow cells to increase production of reticulocytes and red blood cells, about 40 mM of sodium sulfate, and about 10 mM sodium phosphate, said solution having a pH of about 6.2 and being stable at room temperature.

56. A liquid pharmaceutical composition in the form of an aqueous solution comprising from about 25 μg to about 2,500 μg per ml of said solution of an erythropoietin glycoprotein product having the in vivo biological activity of causing bone marrow cells to increase production of reticulocytes and red blood cells, about 40 mM of sodium sulfate, about 10 mM sodium phosphate, 3% mannitol and 10 mM methionine, and having a pH of about 6.2 and being stable at room temperature.

57. A liquid pharmaceutical composition in the form of an aqueous solution comprising from about 25 μg to about 2,500 μg per ml of said solution of an erythropoietin glycoprotein product having the in vivo biological activity of causing bone marrow cells to increase production of reticulocytes and red blood cells, about 30 mM of sodium sulfate, about 40 mM arginine, a buffer, and 3% mannitol, said solution having a pH of about 6.2 and being stable at room temperature.

58. A liquid pharmaceutical composition in the form of an aqueous solution comprising from about 25 μg to about 2,500 μg per ml of said solution of an erythropoietin glycoprotein product having the in vivo biological activity of causing bone marrow cells to increase production of reticulocytes and red blood cells, about 30 mM of sodium sulfate, about 40 mM arginine, and about 3% mannitol, said solution having a pH of about 6.2 and being stable at room temperature.

* * * * *

SEQUENCE LISTING

<160> NUMBER OF SEQ ID NOS: 2

<210> SEQ ID NO 1
<211> LENGTH: 165
<212> TYPE: PRT
<213> ORGANISM: Homo sapiens

<400> SEQUENCE: 1

```
Ala Pro Pro Arg Leu Ile Cys Asp Ser Arg Val Leu Glu Arg Tyr Leu
 1               5                  10                  15

Leu Glu Ala Lys Glu Ala Glu Asn Ile Thr Thr Gly Cys Ala Glu His
            20                  25                  30

Cys Ser Leu Asn Glu Asn Ile Thr Val Pro Asp Thr Lys Val Asn Phe
        35                  40                  45

Tyr Ala Trp Lys Arg Met Glu Val Gly Gln Gln Ala Val Glu Val Trp
    50                  55                  60

Gln Gly Leu Ala Leu Leu Ser Glu Ala Val Leu Arg Gly Gln Ala Leu
65                  70                  75                  80

Leu Val Asn Ser Ser Gln Pro Trp Glu Pro Leu Gln Leu His Val Asp
                85                  90                  95

Lys Ala Val Ser Gly Leu Arg Ser Leu Thr Thr Leu Leu Arg Ala Leu
            100                 105                 110

Gly Ala Gln Lys Glu Ala Ile Ser Pro Pro Asp Ala Ala Ser Ala Ala
        115                 120                 125

Pro Leu Arg Thr Ile Thr Ala Asp Thr Phe Arg Lys Leu Phe Arg Val
    130                 135                 140

Tyr Ser Asn Phe Leu Arg Gly Lys Leu Lys Leu Tyr Thr Gly Glu Ala
145                 150                 155                 160

Cys Arg Thr Gly Asp
                165
```

<210> SEQ ID NO 2
<211> LENGTH: 166
<212> TYPE: PRT
<213> ORGANISM: Homo sapiens -continued

```
<400> SEQUENCE: 2

Ala Pro Pro Arg Leu Ile Cys Asp Ser Arg Val Leu Glu Arg Tyr Leu
 1               5                  10                  15

Leu Glu Ala Lys Glu Ala Glu Asn Ile Thr Thr Gly Cys Ala Glu His
            20                  25                  30

Cys Ser Leu Asn Glu Asn Ile Thr Val Pro Asp Thr Lys Val Asn Phe
         35                  40                  45

Tyr Ala Trp Lys Arg Met Glu Val Gly Gln Gln Ala Val Glu Val Trp
     50                  55                  60

Gln Gly Leu Ala Leu Leu Ser Glu Ala Val Leu Arg Gly Gln Ala Leu
 65                  70                  75                  80

Leu Val Asn Ser Ser Gln Pro Trp Glu Pro Leu Gln Leu His Val Asp
                 85                  90                  95

Lys Ala Val Ser Gly Leu Arg Ser Leu Thr Thr Leu Leu Arg Ala Leu
            100                 105                 110

Gly Ala Gln Lys Glu Ala Ile Ser Pro Pro Asp Ala Ala Ser Ala Ala
        115                 120                 125

Pro Leu Arg Thr Ile Thr Ala Asp Thr Phe Arg Lys Leu Phe Arg Val
    130                 135                 140

Tyr Ser Asn Phe Leu Arg Gly Lys Leu Lys Leu Tyr Thr Gly Glu Ala
145                 150                 155                 160

Cys Arg Thr Gly Asp Arg
                165
```